(12) United States Patent
Izawa et al.

(10) Patent No.: US 9,274,048 B2
(45) Date of Patent: Mar. 1, 2016

(54) GAS CONCENTRATION CALCULATION DEVICE AND GAS CONCENTRATION MEASUREMENT MODULE

(75) Inventors: Toshiyuki Izawa, Hamamatsu (JP); Tadayoshi Murakami, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 644 days.

(21) Appl. No.: 13/578,913

(22) PCT Filed: Feb. 14, 2011

(86) PCT No.: PCT/JP2011/053041
§ 371 (c)(1),
(2), (4) Date: Sep. 18, 2012

(87) PCT Pub. No.: WO2011/102316
PCT Pub. Date: Aug. 25, 2011

(65) Prior Publication Data
US 2013/0003046 A1 Jan. 3, 2013

(30) Foreign Application Priority Data

Feb. 16, 2010 (JP) ................ P2010-031560
Feb. 16, 2010 (JP) ................ P2010-031562
Feb. 16, 2010 (JP) ................ P2010-031564

(51) Int. Cl.
*G01N 21/05* (2006.01)
*G01N 21/3504* (2014.01)

(52) U.S. Cl.
CPC ............ *G01N 21/3504* (2013.01); *G01N 21/05* (2013.01)

(58) Field of Classification Search
CPC G01N 21/3196; G01N 21/3504; G01N 21/39
See application file for complete search history.

(56) References Cited

U.S. PATENT DOCUMENTS

| 5,206,511 A | 4/1993 | Apperson et al. |
| 2005/0146764 A1* | 7/2005 | Deng et al. ................ 359/206 |

(Continued)

FOREIGN PATENT DOCUMENTS

| CN | 101363796 | 2/2009 |
| EP | 1217355 | 6/2002 |

(Continued)

*Primary Examiner* — Casey Bryant
(74) *Attorney, Agent, or Firm* — Drinker Biddle & Reath LLP

(57) ABSTRACT

A device includes a gas cell (10X) configured to form an introduction space (11X) into which a target gas is introduced, an infrared light source (20X) disposed at one end of the gas cell (10X), a modulation mirror (70X) disposed at one end of the gas cell (10X) and configured to reflect or transmit light emitted from the infrared light source (20X), a reflecting mirror (60X) configured to reflect light transmitted through the modulation mirror (70X), a saturated gas chamber (40X), in which a predetermined comparison gas is hermetically enclosed, disposed on an optical path of light transmitted through the modulation mirror (70X), a light receiving unit (30X) disposed at the other end of the gas cell (10X) and configured to receive light reflected by the modulation mirror (70X) and light transmitted through the modulation mirror (70X) and reflected by the reflecting mirror (60X) through the saturated gas chamber (40X), and a calculation circuit (3X) configured to calculate the concentration of the target gas based on received light energy values of the light receiving unit (30X) in each case in which light is reflected or transmitted by the modulation mirror (70X).

32 Claims, 25 Drawing Sheets

(56) References Cited

U.S. PATENT DOCUMENTS

| | | | |
|---|---|---|---|
| 2009/0127478 A1* | 5/2009 | Inoue et al. | 250/504 R |
| 2011/0095189 A1* | 4/2011 | Lall | 250/338.5 |

FOREIGN PATENT DOCUMENTS

| | | | | | |
|---|---|---|---|---|---|
| JP | S50-035283 | 7/1973 | | | |
| JP | S49-099083 | 9/1974 | | | |
| JP | S52-034510 | 9/1977 | | | |
| JP | S52-122172 | 10/1977 | | | |
| JP | S53-098889 | 8/1978 | | | |
| JP | S56-116656 | 2/1980 | | | |
| JP | S61-254835 | 11/1986 | | | |
| JP | 64-3527 | 1/1989 | | | |
| JP | 5-180760 | 7/1993 | | | |
| JP | 3004458 | 11/1994 | | | |
| JP | H8-128956 | 5/1996 | | | |
| JP | 8-271417 | 10/1996 | | | |
| JP | 2001-324446 | 11/2001 | | | |
| JP | 2002-22656 | 1/2002 | | | |
| JP | 2002022656 A | * | 1/2002 | | G01N 21/27 |
| JP | 2003-329585 | 11/2003 | | | |
| JP | 2005-195801 | 7/2005 | | | |
| JP | 2006-23284 | 1/2006 | | | |
| JP | 2007-25143 | 2/2007 | | | |
| JP | 2007-256242 | 10/2007 | | | |
| JP | 2007-256790 | 10/2007 | | | |
| JP | 2008-542693 | 11/2008 | | | |
| TW | 200905184 | 2/2009 | | | |
| WO | 2007/139022 | 12/2007 | | | |

* cited by examiner

*Fig.10*
(A)
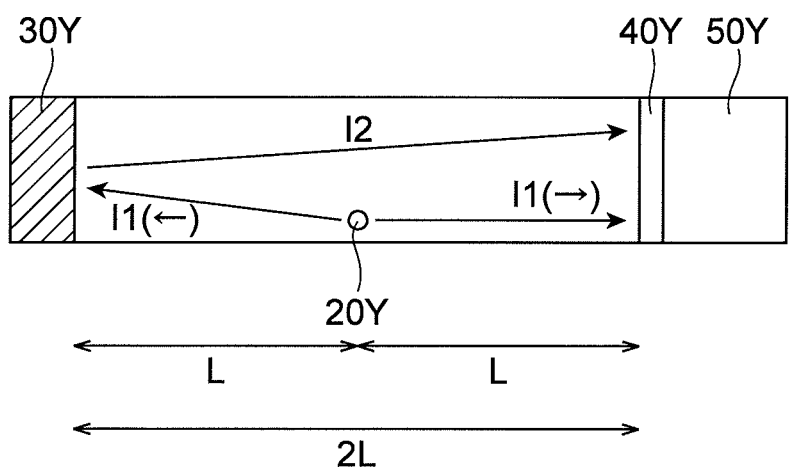
(B)
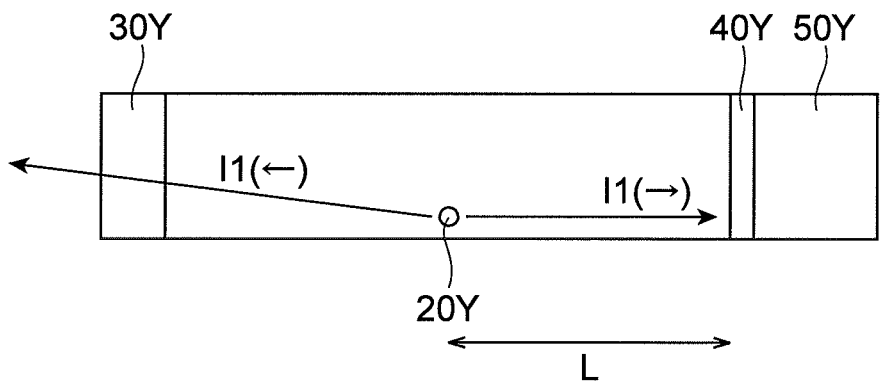

Fig.12

| CO₂ CONCENTRATION (ppm) | I1(→)/I | I1(←)/I | I2/I | Ion/I | Ioff/I | Ion/Ioff |
|---|---|---|---|---|---|---|
| 0 | 0.500 | 0.500 | 0.500 | 1.000 | 0.500 | 2.000 |
| 500 | 0.452 | 0.452 | 0.370 | 0.823 | 0.452 | 1.819 |
| 1000 | 0.409 | 0.409 | 0.274 | 0.684 | 0.409 | 1.670 |
| 1500 | 0.370 | 0.370 | 0.203 | 0.574 | 0.370 | 1.549 |
| 2000 | 0.335 | 0.335 | 0.151 | 0.486 | 0.335 | 1.449 |
| 2500 | 0.303 | 0.303 | 0.112 | 0.415 | 0.303 | 1.368 |
| 3000 | 0.274 | 0.274 | 0.083 | 0.357 | 0.274 | 1.301 |
| 4000 | 0.225 | 0.225 | 0.045 | 0.270 | 0.225 | 1.202 |
| 5000 | 0.184 | 0.184 | 0.025 | 0.209 | 0.184 | 1.135 |

Fig.18
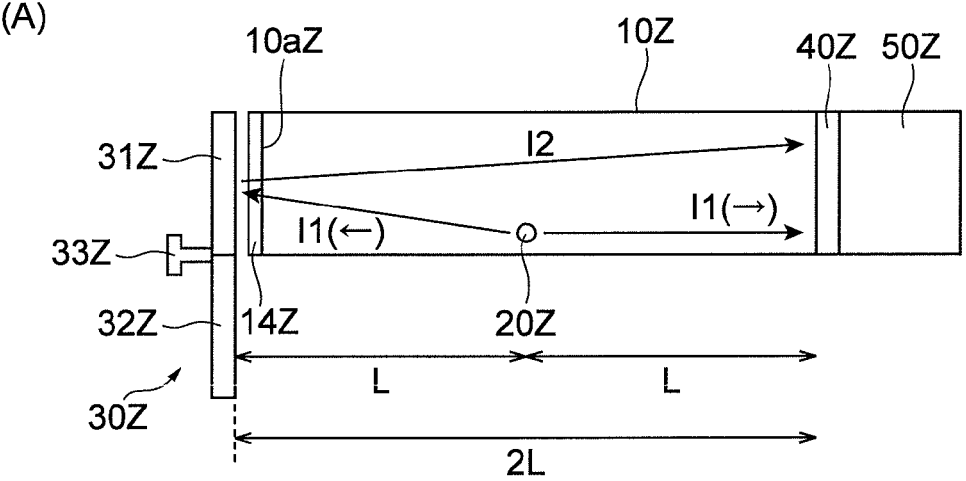
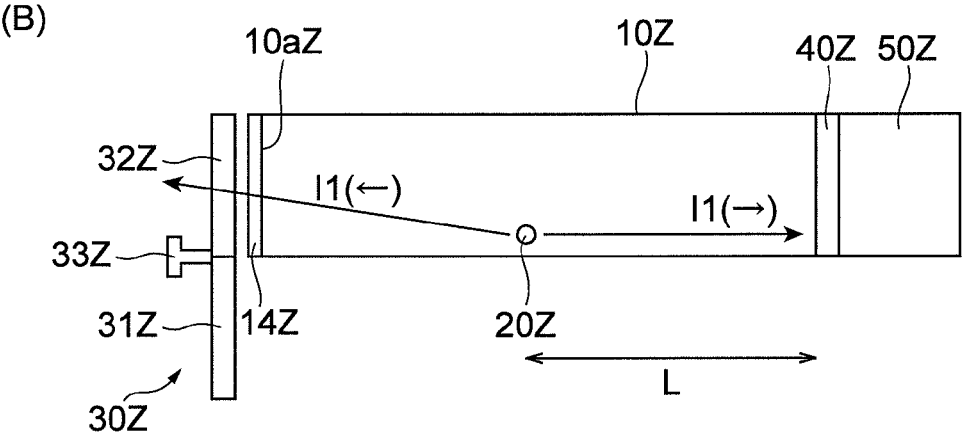

Fig.20

| CO2 CONCENTRATION (ppm) | I1(→)/I | I1(←)/I | I2/I | Ion/I | Ioff/I | Ion/Ioff |
|---|---|---|---|---|---|---|
| 0 | 0.500 | 0.500 | 0.500 | 1.000 | 0.500 | 2.000 |
| 500 | 0.452 | 0.452 | 0.370 | 0.823 | 0.452 | 1.819 |
| 1000 | 0.409 | 0.409 | 0.274 | 0.684 | 0.409 | 1.670 |
| 1500 | 0.370 | 0.370 | 0.203 | 0.574 | 0.370 | 1.549 |
| 2000 | 0.335 | 0.335 | 0.151 | 0.486 | 0.335 | 1.449 |
| 2500 | 0.303 | 0.303 | 0.112 | 0.415 | 0.303 | 1.368 |
| 3000 | 0.274 | 0.274 | 0.083 | 0.357 | 0.274 | 1.301 |
| 4000 | 0.225 | 0.225 | 0.045 | 0.270 | 0.225 | 1.202 |
| 5000 | 0.184 | 0.184 | 0.025 | 0.209 | 0.184 | 1.135 |

Fig.24
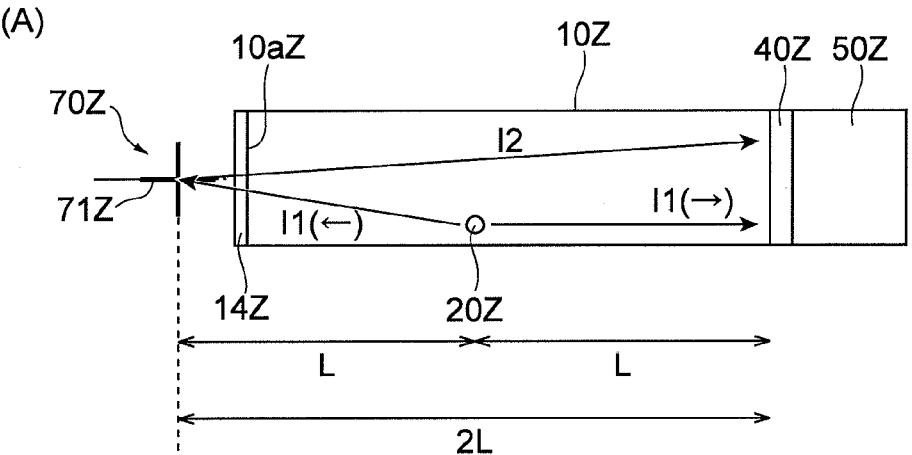
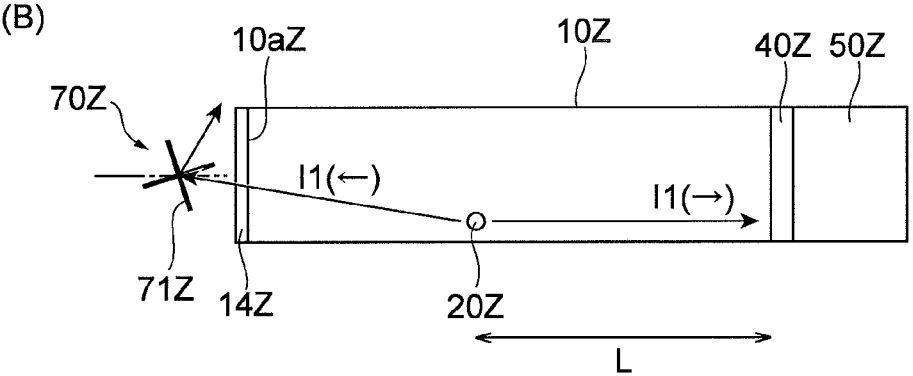

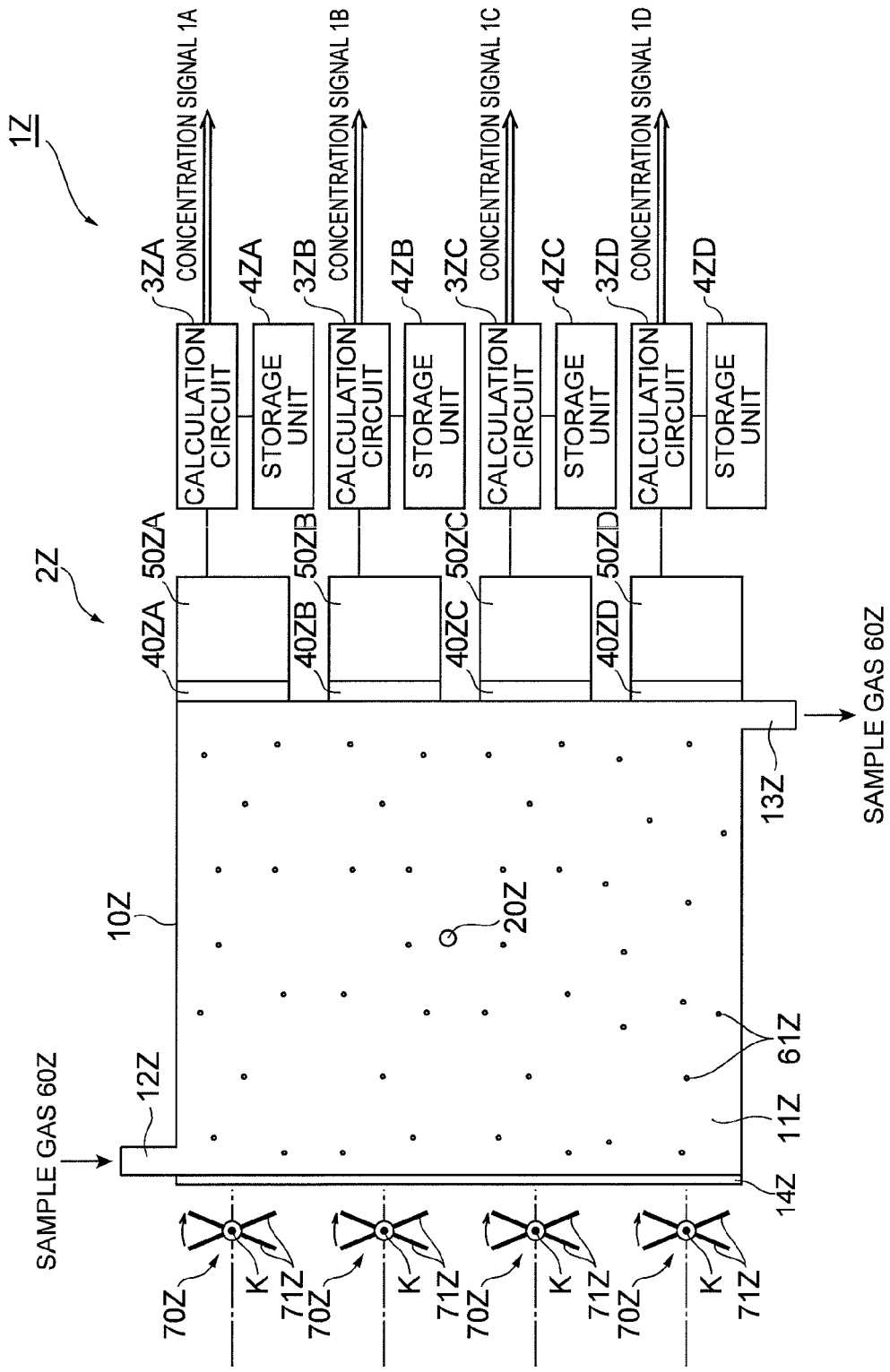

GAS CONCENTRATION CALCULATION DEVICE AND GAS CONCENTRATION MEASUREMENT MODULE

TECHNICAL FIELD

The present invention relates to a gas concentration calculating device and a gas concentration measuring module.

BACKGROUND ART

In the related art, for example, a gas concentration calculating device for calculating a concentration of a gas such as carbon dioxide has been introduced in fields of an air-conditioning system, and so on. As ON/OFF of ventilation is controlled based on calculation results in the gas concentration calculating device, the air-conditioning system is efficiently operated and power consumption is reduced. Such a gas concentration calculating device uses an NDIR (non-dispersive infrared) method, and the NDIR method is a technique of calculating a concentration of a gas based on attenuation upon passage of infrared light through a target gas.

As the gas concentration calculating device using the NDIR method, for example, Patent Document 1 discloses a gas concentration calculating device, in which light from a single light source is emitted into a gas cell, and the light passing through the gas cell is detected by a first detector and a second detector. The first detector detects light passing through an optical path constituted by a region for gas to be measured, and an inert gas region hermetically enclosed in a measuring gas chamber. The second detector detects light passing through an optical path constituted by a region for gas to be measured, and a gas region having the same gas as a gas to be measured, which is hermetically enclosed in a comparison gas chamber. In addition, an increase or decrease in irradiation light quantity is detected by the second detector, and an output of the first detector is calibrated.

Further, Patent Document 2 discloses a gas concentration calculating device for detecting a concentration of a sample gas in a cylinder. Here, a reflecting mirror is installed at a head of a piston reciprocating in the cylinder, and a light source and a detector are disposed at the head of the cylinder to be directed inward with respect to the cylinder. According to the above-mentioned configuration, light emitted from the light source and reflected by the reflecting mirror on the piston is received by the detector. According to the reciprocation of the piston, since an optical path length from the light source to the detector via the reflecting mirror is varied, an energy value received by the detector is varied. Thus, based on a variation in output values output from the detector, a concentration of the sample gas is calculated.

RELATED ART DOCUMENTS

Patent Document

[Patent Document 1] Japanese Patent Laid-open Publication No. 2007-256242
[Patent Document 2] Japanese Patent Laid-open Publication No. H05-180760

SUMMARY OF INVENTION

Technical Problem

In the gas concentration calculating device disclosed Patent Document 1, concentrations of gases are calculated using two separate light receiving elements, which are referred to as a first detector and a second detector. For this reason, individual differences of the light receiving elements themselves (a difference between sensitivity and noise characteristics, a difference with respect to ambient temperatures or a difference with respect to long-term changes of these) exert a bad influence on measurement accuracy of a gas concentration. Since such bad influence is caused by individual differences of the respective light receiving elements, the bad influence is not canceled even when a ratio between output values of both of the light receiving elements is used.

In the gas concentration calculating device of Patent Document 2, since a single light receiving element is used, there is no inconvenience due to the individual differences of the light receiving elements. However, in the technique of Patent Document 2, the reflecting mirror, which is a means for varying an optical path length from the light source to the detector, is installed at the head of the piston, and vertical movement is performed in the same direction as the direction of the optical path. For this reason, in order to realize the measurement with high accuracy, there is a need to temporarily stop the movement of the piston, i.e., the movement of the reflecting mirror, upon measurement. This is because, when the reflecting mirror is moved in the same direction as the direction of the optical path with no stoppage, the optical path length is unstable and measurement with high accuracy becomes impossible. Accordingly, as the movement of the piston is temporarily stopped, a large time deviation between a measurement timing of the reference light and a measurement timing of the signal light occurs. When the time deviation between the measurement timing of the reference light and the measurement timing of the signal light occurs, an error also occurs in the gas concentration calculated based on the ratio of the respective measurement results by the large time deviation.

In addition, in the technique of Patent Document 2, vibrations of the vertical movement or deterioration of the surface of the cylinder exert a bad influence on detection accuracy of the light. Further, since confusion of the signals becomes top and bottom dead centers, a measurement interval depends on a movement speed of the cylinder, and thus, it is difficult to speed up the measurement. When a single light receiving element is used, if the large time deviation between the measurement timing of the reference light and the measurement timing of the signal light occurs, an error also occurs in the gas concentration calculated based on the ratio of the respective measurement results by the time deviation.

Therefore, in consideration of the above-mentioned problems, it is one aspect of the present invention to provide a gas concentration calculating device and a gas concentration measuring module that are capable of preventing inconvenience due to individual differences of the light receiving elements and preventing inconvenience due to instability of the optical path length.

In addition, it is another aspect of the present invention to provide a gas concentration calculating device and a gas concentration measuring module that are capable of preventing inconvenience due to individual differences of the light receiving elements, preventing a decrease in optical detection accuracy due to vibrations of the element for varying the optical path length, and suppressing a decrease in optical detection accuracy due to the measurement time deviation of the light.

Further, it is still another aspect of the present invention to provide a gas concentration calculating device and a gas concentration measuring module that are capable of preventing inconvenience due to individual differences of the light receiving elements, and preventing inconvenience caused as the element for varying the optical path length is moved in the same direction as the direction of the optical path.

Solution to Problem

In order to solve the problems, a gas concentration calculating device according to one aspect of the present invention including a gas concentration measuring module and a gas concentration calculating module and configured to calculate a concentration of a target gas, wherein the gas concentration measuring module includes: a gas cell configured to form an introduction space into which the target gas is introduced; a light source disposed at one end of the gas cell; a reflection switching means disposed at the one end or the other end of the gas cell to reflect or transmit light emitted from the light source; a reflecting means configured to reflect light transmitted through the reflection switching means; a comparison gas cell, in which a predetermined comparison gas is hermetically enclosed, disposed on an optical path of light transmitted through the reflection switching means; and a light receiving means disposed at the other end of the gas cell and configured to receive light emitted from the light source and reflected by the reflection switching means and light emitted from the light source, transmitted through the reflection switching means, passing through the comparison gas cell and reflected by the reflecting means, and wherein the gas concentration calculating module calculates the concentration of the target gas based on received light energy values of the light receiving means in each case in which light is reflected or transmitted by the reflection switching means.

In addition, a gas concentration measuring module according to one aspect of the present invention is a gas concentration measuring module of a gas concentration calculating device configured to calculate a concentration of a target gas, which includes: a gas cell configured to form an introduction space into which the target gas is introduced; a light source disposed at one end of the gas cell; a reflection switching means disposed at the one end or the other end of the gas cell to reflect or transmit light emitted from the light source; a reflecting means for reflecting light transmitted through the reflection switching means; a comparison gas cell, in which a predetermined comparison gas is hermetically enclosed, disposed on an optical path of light transmitted through the reflection switching means; and a light receiving means disposed at the other end of the gas cell, and configured to receive light emitted from the light source and reflected by the reflection switching means and light emitted from the light source, transmitted through the reflection switching means, passing through the comparison gas cell and reflected by the reflecting means.

According to the gas concentration calculating device and the gas concentration measuring module of the present invention, since the light receiving means receives both of the light reflected by the reflection switching means and the light transmitted through the reflection switching means and passing through the comparison gas cell, inconvenience due to individual differences of the light receiving means when the lights in cases in which reflection and transmission are switched by the reflection switching means are separately received by the different light receiving means can be prevented. In addition, since the reflection switching means is disposed at one end or the other end of the gas cell into which the target gas is introduced, i.e., since the reflection switching means is disposed outside the gas cell, there is no variation in optical path length that the light passes through the target gas in the gas cell in each case in which reflection and transmission are switched by the reflection switching means. For this reason, inconvenience due to instability of the optical path length of the light passing through the target gas can be prevented.

In addition, in the present invention, the reflection switching means may be a reflectance modulation means for electrically modulating a reflectance with respect to light emitted from the light source to switch reflection and transmission of light.

In this case, a means for generating a difference in received light energy values of the light received by the light receiving means is the reflectance modulation means, and an operation of the reflectance modulation means is performed by electric control of the reflectance. Accordingly, since there is no vibration or the like to generate a difference in received light energy values and thus no position difference, additional noise, or the like due to the vibration, a decrease in optical detection accuracy of the gas concentration measuring module can be prevented.

In addition, as the reflectance modulation means electrically controls the reflectance, the reflectance switching can be rapidly performed. Accordingly, the time deviation in the optical measurement timing of the light received by the light receiving means is negligible or remarkably short, and thus, pseudo-simultaneous measurement can be performed.

In addition, as the reflectance modulation means having such effects, a spatial light modulator (SLM) or a liquid crystal optical element is preferable.

In addition, in the present invention, the reflection switching means may be a rotary mechanism configured to switch reflection and transmission by rotation with respect to light emitted from the light source.

In this case, a means for generating a difference in received light energy values of the lights received by the light receiving means is the rotary mechanism. Even when the rotary mechanism is rotated, since the rotary mechanism is disposed outside the gas cell, there is no variation in optical path length that the light passes through the target gas in the gas cell in each case in which reflection and transmission are switched. Accordingly, for example, unlike the case of Patent Document 2, since the optical path length is stable, there is no need to temporarily stop the rotary mechanism. As a result, inconvenience such as generation of the large time deviation in the optical measurement timing due to temporary movement stoppage of the rotary mechanism can be prevented.

In addition, in the present invention, the rotary mechanism may be a rotating mirror constituted by a reflecting plate and a hole.

In this case, a simple configuration can be provided by the rotating mirror constituted by the reflecting plate and the hole.

In addition, in the present invention, the reflecting means may include a plurality of reflecting surfaces having different angles, and sequentially reflect light transmitted through the reflection switching means at the plurality of reflecting surfaces to allow transmission of the light through the comparison gas cell upon each reflection of the reflecting surfaces.

In this case, since the light reflected by the reflecting surface of the reflecting means passes through the comparison gas cell a plurality of times, the optical path passing through the comparison gas cell can be increased. For this reason, characteristics of the light emitted from the light source can be sufficiently varied in the comparison gas cell. In addition, since the light passes through the comparison gas cell a plurality of times, the optical path length of the light passing through the comparison gas cell can be increased by a compact comparison gas cell, with no increase in size of the comparison gas cell.

In addition, in the present invention, the predetermined comparison gas may be the same kind of saturated gas as the target gas. As the band pass filter and the comparison gas are changed to correspond to the target gas, a plurality of kinds of gases can be measured.

In this case, using variation in characteristics when the light passes through the same kind of saturated gas as the target gas, a difference in received light energy values by the light receiving means can be generated.

In addition, in the present invention, a band pass filter disposed on an optical path between the light source and the light receiving means and configured to transmit light having a predetermined wavelength only may be further provided.

The waveband of the received light can become the same waveband by the band pass filter, and a decrease in optical detection accuracy can be prevented as the lights having different wavebands are received.

In addition, in the present invention, the light source may emit infrared rays.

Using a phenomenon that the energy is attenuated when the infrared rays pass through the target gas, the concentration of the target gas can be calculated.

In addition, in the present invention, the target gas may be carbon dioxide.

Using a phenomenon that the energy is attenuated when the light passes through the carbon dioxide, the concentration of the target gas can be calculated.

The gas concentration measuring module having a plurality of light receiving means corresponding to different target gases, and the plurality of gas concentration calculating modules corresponding to the plurality of light receiving means may be provided.

In this case, the band pass filter, the comparison gas and the light receiving unit are increased in number to enable simultaneous measurement of a plurality of gases. In this case, the band pass filter may be disposed on the front face of the light receiving unit. In addition, as the plurality of gas concentration measuring modules corresponding to different target gases are provided, concentrations of the plurality of gases can be simultaneously and accurately calculated.

In addition, a gas concentration calculating device according to another aspect of the present invention including a gas concentration measuring module and a gas concentration calculating module and configured to calculate a concentration of a target gas, wherein the gas concentration measuring module includes: a gas cell configured to form an introduction space into which the target gas is introduced; a light source disposed in the gas cell; a reflectance modulation means disposed at one end of the gas cell and configured to electrically modulate a reflectance with respect to light emitted from the light source; and a light receiving means disposed at the other end of the gas cell and configured to receive a direct light directly emitted from the light source and a reflection light emitted from the light source and reflected by the reflectance modulation means, and wherein the gas concentration calculating module calculates the concentration of the target gas based on a ratio of received light energy values of the light receiving means in each case in which the reflectance is electrically modulated by the reflectance modulation means.

In addition, a gas concentration measuring module according to another aspect of the present invention is a gas concentration measuring module of a gas concentration calculating device configured to calculate a concentration of a target gas, which includes: a gas cell configured to form an introduction space into which the target gas is introduced; a light source disposed in the gas cell; a reflectance modulation means disposed at one end of the gas cell and configured to electrically modulate a reflectance with respect to light emitted from the light source; and a light receiving means disposed at the other end of the gas cell and configured to receive a direct light directly emitted from the light source and a reflection light emitted from the light source and reflected by the reflectance modulation means.

According to the gas concentration calculating device and the gas concentration measuring module of the present invention, since the light receiving means receives both of the direct light and the reflection light, inconvenience due to individual differences of the light receiving means when the direct light and the reflection light are received by the different light receiving means or when the light in each case in which the reflectance is electrically modulated by the reflectance modulation means are separately received by the different light receiving means can be prevented.

In addition, in the present invention, a means for generating variation in optical path length or a difference in received light energy values of the lights received by the light receiving means is the reflectance modulation means, and an operation of the reflectance modulation means is performed by electrical control of the reflectance. Accordingly, since there is no vibration or the like to generate variation in optical path length or a difference in received light energy values and thus no position difference, additional noise, or the like due to the vibration, a decrease in optical detection accuracy of the gas concentration measuring module can be prevented.

In addition, as the reflectance modulation means electrically modulates the reflectance, the reflectance switching can be rapidly performed. Accordingly, the time deviation in the optical measurement timing of the light received by the light receiving means is negligible or remarkably short, and thus, pseudo-simultaneous measurement can be performed.

As described above, according to the present invention, generation of inconvenience due to individual differences of the light receiving means, an error due to the vibration, and an error due to the time deviation can be prevented. In addition, as the reflectance modulation means having such effects, an electro-optic device (EO device) or a liquid crystal optical element is preferable.

In addition, in the present invention, a band pass filter disposed on an optical path between the light source and the light receiving means and configured to transmit light having a predetermined wavelength only may be further provided.

The waveband of the received light can become the same waveband by the band pass filter, and a decrease in optical detection accuracy can be prevented as the lights having different wavebands are received.

In addition, in the present invention, the light source may emit infrared rays.

Using a phenomenon that the energy is attenuated when the infrared rays pass through the target gas, the concentration of the target gas can be calculated.

In addition, in the present invention, the target gas may be carbon dioxide.

Using a phenomenon that the energy is attenuated when the light passes through the carbon dioxide, the concentration of the target gas can be calculated.

In addition, in the present invention, a storage means for previously storing a database or an approximate equation showing a correlation between the concentration of the target gas and the ratio may be further provided, and the gas concentration calculating module may calculate the concentration corresponding to the ratio based on the database or the approximate equation.

According to the present invention, the concentration of the target gas can be accurately calculated based on the prepared database or approximate equation.

In addition, in the present invention, the gas concentration measuring module having a plurality of light receiving means corresponding to different target gases, and the plurality of gas concentration calculating modules corresponding to the plurality of light receiving means may be provided.

According to the present invention, as the plurality of gas concentration measuring modules corresponding to different target gases are provided, concentrations of the plurality of gases can be simultaneously and accurately calculated.

In addition, a gas concentration calculating device according to still another aspect of the present invention including a gas concentration measuring module and a gas concentration calculating module and configured to calculate a concentration of a target gas, wherein the gas concentration measuring module includes: a gas cell configured to form an introduction space into which the target gas is introduced; a light source disposed in the gas cell; a rotary mechanism disposed at one end of the gas cell and configured reflect or transmit light emitted from the light source by rotation thereof; and a light receiving means disposed at the other end of the gas cell and configured to receive a direct light directly emitted from the light source and a reflection light emitted from the light source and reflected by the rotary mechanism, and wherein the gas concentration calculating module calculates the concentration of the target gas based on a ratio of received light energy values of the light receiving means in each case in which the light is reflected or transmitted by the rotary mechanism, and the rotary mechanism performs the rotation in a direction different from a direction of an optical path from the light source to the light receiving means.

In addition, a gas concentration measuring module according to still another aspect of the present invention is a gas concentration measuring module of a gas concentration calculating device configured to calculate a concentration of a target gas, which includes: a gas cell configured to form an introduction space into which the target gas is introduced; a light source disposed in the gas cell; a rotary mechanism disposed at one end of the gas cell and configured to reflect or transmit light emitted from the light source by rotation thereof; and a light receiving means disposed at the other end of the gas cell and configured to receive a direct light directly emitted from the light source and a reflection light emitted from the light source and reflected by the rotary mechanism, wherein the rotary mechanism performs the rotation in a direction different from a direction of an optical path from the light source to the light receiving means.

According to the gas concentration calculating device and the gas concentration measuring module of the present invention, since the light receiving means receives both of the direct light and the reflection light, inconvenience due to individual differences of the light receiving means when the direct light and the reflection light are received by the different light receiving means or when the lights in each case in which the light is reflected or transmitted by the rotary mechanism are separately received by the different light receiving means can be prevented.

In addition, in the present invention, a means for generating a difference in optical path length or a difference in received light energy values of the light received by the light receiving means is the rotary mechanism, and the rotary mechanism performs the rotation in a direction different from a direction of the optical path from the light source to the light receiving means, allowing reflection or transmission of the light. Here, "the rotation in the direction different from the direction of the optical path" means, for example, that a rotation axis of the rotary mechanism can be disposed in the same direction as the optical path. That is, in order to generate the variation in optical path length or the difference in received light energy values, there is no need to perform movement of the rotary mechanism in the direction of the optical path, and for this reason, even when the rotary mechanism is rotated, there is no variation in absolute distance between the rotary mechanism and the light receiving means. Accordingly, for example, unlike the case of Patent Document 2, since the optical path length is stable, there is no need to temporarily stop the rotary mechanism. As a result, generation of the large time deviation in the optical measurement timing due to the temporary movement stoppage of the rotary mechanism can be prevented.

As described above, according to the present invention, inconvenience due to the individual differences of the light receiving means or inconvenience due to movement of the element for varying the optical path length in the same direction as the direction of the optical path can be avoided.

In addition, in the present invention, the rotary mechanism may be a rotating mirror constituted by a reflecting plate and a hole.

A simple configuration can be provided by the rotating mirror constituted by the reflecting plate and the hole.

In addition, in the present invention, the rotating mirror may perform the rotation in a direction substantially perpendicular to the direction of the optical path from the light source to the light receiving means.

For example, as the rotation axis of the rotating mirror is disposed in substantially the same direction as the optical path, the rotating mirror can be rotated in a direction substantially perpendicular to the direction of the optical path. Accordingly, reflection and transmission of the light can be clearly switched.

In addition, in the present invention, the rotary mechanism may be constituted by a micro-electro-mechanical system (MEMS) actuator and a mirror.

In this case, as the MEMS actuator is used, rapid rotation becomes possible while suppressing vibrations upon rotation. Accordingly, a decrease in optical detection accuracy due to the vibrations can be prevented. Further, as the MEMS actuator is rapidly rotated, switching of reflection and transmission of the light can be rapidly performed, the time deviation in the optical measurement timing of the light received by the light receiving means is negligible or remarkably short, and thus, pseudo-simultaneous measurement can be performed.

In addition, in the present invention, a band pass filter disposed on an optical path between the light source and the light receiving means and configured to transmit of light having a predetermined wavelength only may be further provided.

The waveband of the received light can become the same waveband by the band pass filter, and a decrease in optical detection accuracy can be prevented as the lights having different wavebands are received.

In addition, in the present invention, the light source may emit infrared rays.

Using a phenomenon that the energy is attenuated when the infrared rays pass through the target gas, the concentration of the target gas can be calculated.

In addition, in the present invention, the target gas may be carbon dioxide.

Using a phenomenon that the energy is attenuated when the light passes through the carbon dioxide, the concentration of the target gas can be calculated. In addition, the gas is not limited to carbon dioxide. Further, by increasing only the band pass and the light receiving unit in number, a plurality of gases can be measured.

In addition, in the present invention, a storage means for previously storing a database or an approximate equation showing a correlation between the concentration of the target gas and the ratio may be further provided, and the gas concentration calculating module calculates the concentration corresponding to the ratio based on the database or the approximate equation.

According to the present invention, based on the prepared database or approximate equation, the concentration of the target gas can be accurately calculated.

In addition, in the present invention, the gas concentration measuring module having a plurality of light receiving means corresponding to different target gases, and the plurality of gas concentration calculating modules corresponding to the plurality of light receiving means may be provided.

According to the present invention, as the plurality of gas concentration measuring modules corresponding to different target gases are provided, concentrations of a plurality of gases can be simultaneously and accurately calculated.

Advantageous Effects of Invention

According to one aspect of the present invention, it is possible to provide a gas concentration calculating device and a gas concentration measuring module that are capable of preventing inconvenience due to individual differences of the light receiving elements and preventing inconvenience due to instability of the optical path length.

In addition, according to another aspect of the present invention, it is possible to provide a gas concentration calculating device and a gas concentration measuring module that are capable of preventing inconvenience due to individual differences of the light receiving elements, preventing a decrease in optical detection accuracy due to vibrations of the element for generating variation in the optical path length or a difference in received light energy values, and suppressing a decrease in optical detection accuracy due to the measurement time deviation of the light.

Further, according to another aspect of the present invention, it is possible to provide a gas concentration calculating device and a gas concentration measuring module that are capable of preventing inconvenience due to individual differences of the light receiving elements, and preventing inconvenience caused because the element for varying the optical path length is moved in the same direction as the direction of the optical path.

BRIEF DESCRIPTION OF DRAWINGS

FIG. 10 is a view for describing a structure for generating a difference in an optical path length or a received light energy value;

FIG. 12 is a view showing one example of a database stored in the storage unit 4Y;

FIG. 18 is a view for describing a structure for generating a difference in an optical path length or a received light energy value in the fifth embodiment;

FIG. 20 is a view showing one example of a database stored in the storage unit 4Z;

FIG. 24 is a view for describing a structure for generating a difference in an optical path length or a received light energy value in the sixth embodiment; and FIG. 25 is a schematic cross-sectional view showing a variant of the gas concentration calculating device 1Z.

DESCRIPTION OF EMBODIMENTS

Figure 1:
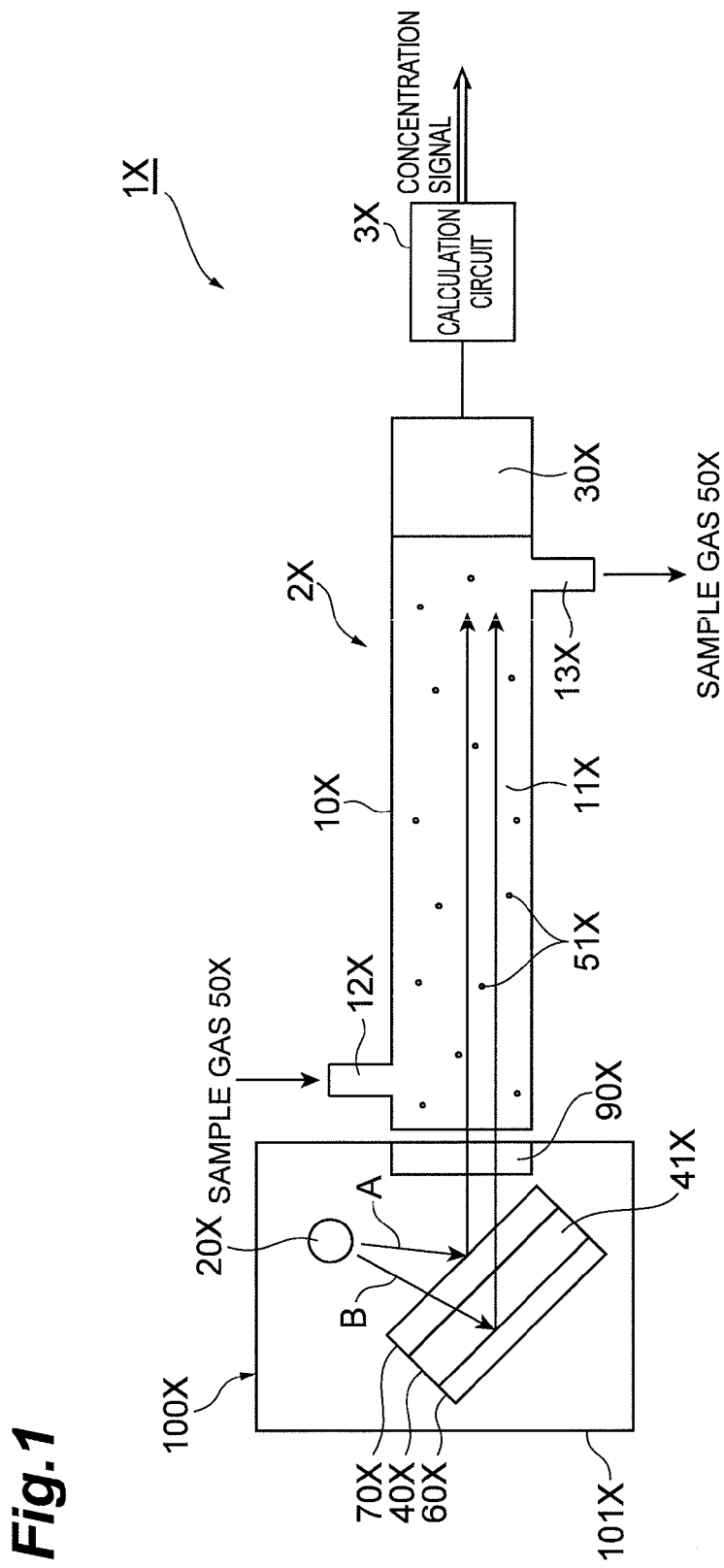
FIG. 1 is a schematic cross-sectional view of a gas concentration calculating device 1X according to a first embodiment.

Hereinafter, exemplary embodiments of a gas concentration calculating device and a gas concentration measuring module according to the present invention will be described in detail with reference to the accompanying drawings. In addition, like elements in the description of the drawings are designated by like reference numerals, and description thereof will not be repeated.

[First Embodiment]

In a first embodiment, a modulation mirror 70X is disposed at one end of a gas cell 10X (at which an infrared light source 20X is disposed).

(Overall Configuration of Gas Concentration Calculating Device 1X)

First, an overall configuration of the gas concentration calculating device 1X according to a first embodiment will be described. FIG. 1 is a schematic cross-sectional view showing the gas concentration calculating device 1X. The gas concentration calculating device 1X includes a gas concentration measuring module 2X configured to receive light from an infrared light source 20X (corresponding to "a light source" of the claims) and measure an energy value thereof, and a calculation circuit 3X (corresponding to "a gas concentration calculating module" of the claims) configured to calculate a gas concentration based on a measurement result by the gas concentration measuring module 2X, calculating a concentration of a target gas. The gas concentration calculated by the calculation circuit 3X is output to a control device (not shown) to be used to control, for example, an air-conditioning system, or the like. In addition, in the first embodiment, the case in which carbon dioxide in a sample gas 50 introduced into the gas concentration measuring module 2X is used as a target gas for concentration calculation will be described.

The gas concentration measuring module 2X includes a gas cell 10X, a reflection switching unit 100X including the infrared light source 20X, and a light receiving unit 30X (corresponding to "a light receiving means" of the claims).

The gas cell 10X forms an introduction space 11X into which the sample gas 50X is introduced. The gas cell 10X has a gas introduction unit 12X installed at one end side of the gas cell 10X and configured to introduce the sample gas 50X into the introduction space 11X, and a gas discharge unit 13X installed at the other end side of the gas cell 10X and configured to discharge the sample gas 50X in the introduction space 11X to the outside. As the gas introduction unit 12X or the gas discharge unit 13X, a plurality of holes formed in an inner wall (for example, a top portion or a bottom portion) of the gas cell may be used.

The reflection switching unit 100X is disposed at one end of the gas cell 10X, and includes the infrared light source 20X, the modulation mirror 70X (corresponding to "a reflection switching means or a reflectance modulation means" of the claims), a saturated gas chamber 40X (corresponding to "a comparison gas cell" of the claims) in which a saturated gas 41X (corresponding to "a comparison gas" of the claims) is hermetically enclosed, a reflecting mirror 60X (corresponding to "a reflecting means" of the claims), and a band pass filter 90X.

The infrared light source 20X is configured to emit infrared rays. In the first embodiment, a light source configured to emit light having a wavelength range of 4.2 μm to 4.3 μm is used as the infrared light source 20X. The infrared rays from the infrared light source 20X are absorbed and attenuated by carbon dioxide molecules 51X in the sample gas 50X.

The modulation mirror 70X is configured to electrically modulate a reflectance with respect to the light emitted from the infrared light source 20X. Here, the modulation mirror 70X electrically modulates the reflectance to totally reflect or totally transmit the light emitted from the infrared light source 20X. The light emitted by the modulation mirror 70X is emitted toward a light receiving unit 30X. In addition, in the first embodiment, for example, a liquid crystal optical element or a spatial light modulator (SLM) is employed as the modulation mirror 70X. In addition to this, the other techniques of controlling a reflectance at a dielectric substance, a metal mesh, or the like may be used.

The reflecting mirror 60X is configured to reflect the light transmitted through the modulation mirror 70X toward the light receiving unit 30X. Here, the saturated gas chamber 40X is disposed between the modulation mirror 70X and the reflecting mirror 60X. For this reason, the light transmitted through the modulation mirror 70X passes through the saturated gas 41X in the saturated gas chamber 40X to be reflected by the reflecting mirror 60X. The light reflected by the reflecting mirror 60X passes through the saturated gas 41X again, and is transmitted through the modulation mirror 70X to enter the light receiving unit 30X.

The saturated gas 41X hermetically enclosed in the saturated gas chamber 40X is the same kind of saturated gas as the sample gas 50X.

The band pass filter 90X is disposed on an optical path between the infrared light source 20X and the light receiving unit 30X, and configured to pass only the light having a predetermined wavelength therethrough. In the first embodiment, the band pass filter 90X is disposed in the reflection switching unit 100X, and configured to transmit only the light having a wavelength range of 4.2 μm to 4.3 μm. In addition, when the band pass filter 90X is not installed in the reflection switching unit 100X, for example, the band pass filter may be installed between the light receiving unit 30X and the gas cell 10X. In addition, for example, an inert gas, which is inert with respect to the infrared rays emitted from the infrared light source 20X, or the sample gas 50X is filled in a housing 101X of the reflection switching unit 100X.

The light receiving unit 30X is a light receiving element disposed at the other end of the gas cell 10X and configured to receive both of the light emitted from the infrared light source 20X and reflected by the modulation mirror 70X and the light emitted from the infrared light source 20X and transmitted through the modulation mirror 70X to pass through the saturated gas chamber 40X. That is, one light receiving unit 30X receives both of the light passing through the saturated gas chamber 40X and the light that does not pass through the saturated gas chamber 40X. Accordingly, in comparison with the case in which a plurality of light receiving means are used to receive a plurality of kinds of lights, respectively, there is no bad effect due to individual differences of the light receiving means.

(Structure for Generating Difference in Received Light Energy Values)

A difference in received light energy values of the lights received by the light receiving unit 30X will be described. Here, as control of reflection or transmission of the light in the modulation mirror 70X is performed, the difference in received light energy values of the lights received by the light receiving unit 30X occurs.

Specifically, when the modulation mirror 70X is controlled in a state in which the light is reflected by the modulation mirror 70X, along an optical path A shown by an arrow of FIG. 1, the light emitted from the infrared light source 20X is reflected by the modulation mirror 70X, and the reflected light passes through the sample gas 50X in the gas cell 10X to enter the light receiving unit 30X.

Meanwhile, when the modulation mirror 70X is controlled in a state in which the light is transmitted through the modulation mirror 70X, along an optical path B shown by an arrow of FIG. 1, the light emitted from the infrared light source 20X is transmitted through the modulation mirror 70X and passes through the saturated gas chamber 40X to be reflected by the reflecting mirror 60X. The light reflected by the reflecting mirror 60X passes through the saturated gas chamber 40X again to be transmitted through the modulation mirror 70X, and further passes through the sample gas 50X in the gas cell 10X to enter the light receiving unit 30X.

As described above, when the modulation mirror 70X is controlled to be in the transmissive state, the optical path length is increased by an extent that the light passes through the saturated gas chamber 40X, in comparison with the case in which the modulation mirror 70X is controlled to be in the reflective state. In addition, as the infrared beam passes through the saturated gas 41X hermetically enclosed in the saturated gas chamber 40X, energy of the light is absorbed by the saturated gas. Accordingly, when the light receiving unit 30X receives the light passing through the saturated gas chamber 40X (when the light is transmitted through the modulation mirror 70X), the light having a low energy value is received, in comparison with the case in which the light not passing through the saturated gas chamber 40X is received (when the light is reflected by the modulation mirror 70X).

As described above, in the first embodiment, variation in received light energy values is electrically performed by the modulation mirror 70X. For this reason, since the modulation mirror is compact and further a movable part can be removed, bad effects such as a position difference, additional noise, or the like due to the vibrations are removed, and accuracy is improved. Further, a modulation speed is largely increased in comparison with a mechanical type.

(Concentration Calculation Processing of Carbon Dioxide)

Next, the processing of calculating the concentration of the carbon dioxide using the calculation circuit 3X from the received light energy values of the lights received by the light receiving unit 30X will be described. The light receiving unit 30X outputs the received light energy value of the light reflected by the modulation mirror 70X and passing through only the sample gas 50X and the received light energy value of the light transmitted through the modulation mirror 70X and passing through the saturated gas chamber 40X and the sample gas 50X to the calculation circuit 3X. The calculation circuit 3X can calculate the concentration of the carbon dioxide in the sample gas 50X by calculating an increase or decrease in an emitted amount based on the received light energy values of the lights passing through the saturated gas chamber 40X and the sample gas 50X and correcting the received light energy value of the light passing through only the sample gas 50X. In addition, in a sequence of calculating the gas concentration based on the two received light energy values, for example, as disclosed in Patent Document 1, the calculation can be performed using a gas correlation method, which is well-known in the related art, and detailed description thereof will be omitted.

(Operations and Effects of First Embodiment)

Next, operations and effects of the gas concentration calculating device 1X according to the first embodiment will be described. According to the gas concentration calculating device 1X of the first embodiment, since the light receiving unit 30X receives both of the light reflected by the modulation mirror 70X and the light transmitted through the modulation mirror 70X and passing through the saturated gas chamber 40X, inconvenience due to the individual differences of the light receiving unit 30X when the lights are separately received by the different light receiving units 30X, respectively, when the reflection and transmission are switched by the modulation mirror 70X is prevented. In addition, since the modulation mirror 70X is disposed at one end of the gas cell 10X into which the sample gas 50X is introduced, i.e., since the modulation mirror 70X is disposed outside the gas cell 10X, there is no variation in optical path length that the respective lights pass through the sample gas 50X when the reflection and transmission are switched by the modulation mirror 70X. For this reason, inconvenience due to instability of the optical path length of the light passing through the sample gas 50X can be prevented.

In addition, in the first embodiment, a means for generating variation in optical path length or a difference in received light energy values of the lights received by the light receiving unit 30X is the modulation mirror 70X, and an operation of the modulation mirror 70X is performed by electrical control of the reflectance. Accordingly, since there is no vibration or the like to generate a difference in optical path length or a difference in received light energy value and thus no position difference, additional noise, or the like due to the vibration, a decrease in optical detection accuracy of the gas concentration measuring module 2X can be prevented.

In addition, as the modulation mirror 70X electrically controls the reflectance, the reflectance switching can be rapidly performed. Accordingly, the time deviation in the optical measurement timing of the light received by the light receiving unit 30X is negligible or remarkably short, and thus, pseudo-simultaneous measurement can be performed.

In addition, as the modulation mirror 70X having such effects, a spatial light modulator (SLM) or a liquid crystal optical element is preferable.

Further, using variation in characteristics when the light emitted from the infrared light source 20X passes through the same kind of saturated gas 41X as the sample gas 50X, a difference in received light energy values can be generated by the light receiving unit 30X.

Furthermore, the waveband of the received light can become the same waveband by the band pass filter 90X, and a decrease in optical detection accuracy can be prevented as the lights having different wavebands are received.

In addition, as the infrared light source 20X emits the infrared rays, using a phenomenon that the energy is attenuated by the carbon dioxide when the infrared rays pass through the sample gas 50X, the concentration of the carbon dioxide in the sample gas 50X can be calculated.

Further, using a phenomenon that the energy is attenuated when the infrared light emitted from the infrared light source 20X passes through the carbon dioxide in the sample gas 50X, the concentration of the carbon dioxide in the sample gas 50X can be calculated. In addition, as the wavelength of the used light is selected by the band pass filter and the comparison gas is provided as a measuring gas, the kind of gas that can be measured is not limited to the carbon dioxide but, obviously, may be arbitrarily determined.

[Second Embodiment]

In a second embodiment, the modulation mirror 70X is disposed at the other end side of the gas cell 10X (at which the light receiving unit 30X is disposed). In addition, like elements in the first embodiment are designated by like reference numerals and detailed description thereof will not be repeated.

(Overall Configuration of Gas Concentration Calculating Device 1XA)

Figure 2:
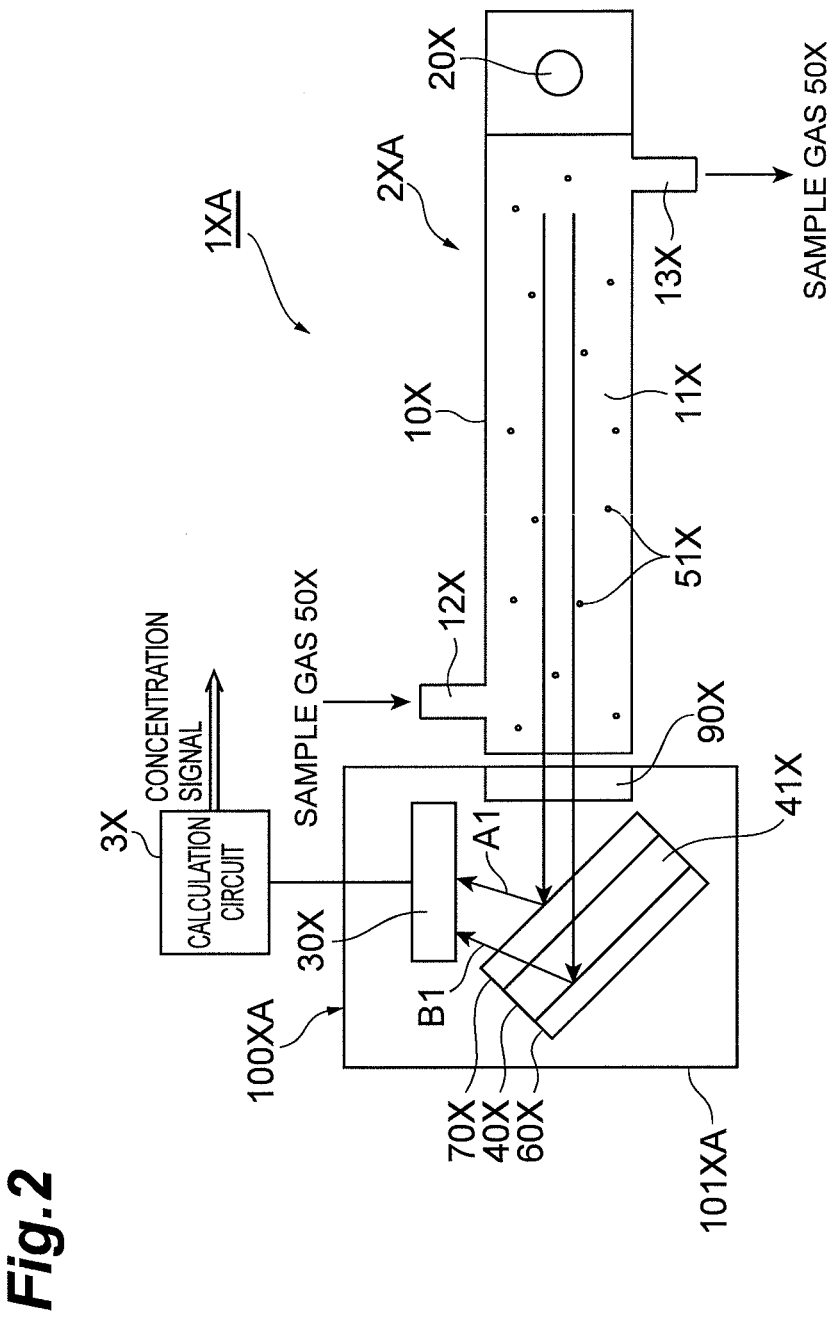
FIG. 2 is a schematic cross-sectional view of a gas concentration calculating device 1XA according to a second embodiment.

First, an overall configuration of the gas concentration calculating device 1XA according to the second embodiment will be described. FIG. 2 is a schematic cross-sectional view showing the gas concentration calculating device 1XA. The gas concentration calculating device 1XA includes a gas concentration measuring module 2XA configured to receive light from an infrared light source 20X (corresponding to "a light source" of the claims) to measure an energy value thereof, and a calculation circuit 3X (corresponding to "a gas concentration calculating module" of the claims) configured to calculate a gas concentration based on the measurement result by the gas concentration measuring module 2XA, calculating the concentration of the target gas. The gas concentration calculated by the calculation circuit 3X is output to a control device (not shown) to be used to control, for example, an air-conditioning system, and so on. In addition, in the second embodiment, the case in which the carbon dioxide in the sample gas 50X introduced into the gas concentration measuring module 2XA is provided as a target gas for concentration calculation will be described.

The gas concentration measuring module 2XA includes a gas cell 10X, a reflection switching unit 100XA, and an infrared light source 20X.

The infrared light source 20X is disposed at one end of the gas cell 10X and configured to emit infrared rays. In the second embodiment, a light source configured to emit light having a wavelength range of 4.2 µm to 4.3 µm is used as the infrared light source 20X. The infrared rays from the infrared light source 20X are absorbed and attenuated by the carbon dioxide molecules 51X in the sample gas 50X.

The reflection switching unit 100XA is disposed at the other end of the gas cell 10X, and includes a light receiving unit 30×(corresponding to "a light receiving means" of the claims), a modulation mirror 70X (corresponding to "a reflection switching means or a reflectance modulation means" of the claims), a saturated gas chamber 40X (corresponding to "a comparison gas cell" of the claims) into which the saturated gas 41X (corresponding to "a comparison gas" of the claims) is hermetically enclosed, a reflecting mirror 60X (corresponding to "a reflecting means" of the claims), and a band pass filter 90X.

The modulation mirror 70X is configured to electrically modulate the reflectance with respect to the light emitted from the infrared light source 20X and passing through the sample gas 50X. Here, the modulation mirror 70X electrically modulates the reflectance to perform total reflection or total transmission of the light emitted from the infrared light source 20X and passing through the sample gas 50X. The light reflected by the modulation mirror 70X is emitted toward the light receiving unit 30X. In addition, in the second embodiment, for example, a liquid crystal optical element or a spatial light modulator (SLM) is employed as the modulation mirror 70X. In addition to this, another method of controlling a reflectance at a dielectric substance, a metal mesh, or the like may be used.

The reflecting mirror 60X is configured to reflect the light passing through the modulation mirror 70X toward the light receiving unit 30X. Here, the saturated gas chamber 40X is disposed between the modulation mirror 70X and the reflecting mirror 60X. For this reason, the light transmitted through the modulation mirror 70X passes through the saturated gas 41X in the saturated gas chamber 40X to be reflected by the reflecting mirror 60X. The light reflected by the reflecting mirror 60X passes through the saturated gas 41X again, and is transmitted through the modulation mirror 70X to enter the light receiving unit 30X.

The light receiving unit 30X is a light receiving element configured to receive both of the light emitted from the infrared light source 20X to pass through the sample gas 50X and reflected by the modulation mirror 70X and the light emitted from the infrared light source 20X to pass through the sample gas 50X to be reflected by the reflecting mirror 60X and pass through the saturated gas chamber 40X. That is, one light receiving unit 30X receives both of the light passing through the saturated gas chamber 40X and the light not passing through the saturated gas chamber 40X. Accordingly, there is no bad effect due to individual differences of the light receiving means, in comparison with the case in which a plurality of light receiving means are used to receive a plurality of kinds of lights, respectively.

In addition, for example, an inert gas, which is inert with respect to the infrared rays emitted from the infrared light source 20X, or the sample gas 50X, is filled in the housing 101XA of the reflection switching unit 100XA.

(Structure for Generating Difference in Received Light Energy Values)

A difference between the received light energy values of the lights received by the light receiving unit 30X will be described. Here, as control of the reflection or the transmission of the light in the modulation mirror 70X is performed, a difference in received light energy values of the lights received by the light receiving unit 30X is generated.

Specifically, when the modulation mirror 70X is controlled in a state in which the light is reflected by the modulation mirror 70X, along the optical path A1 shown by an arrow in FIG. 2, the light emitted from the infrared light source 20X passes through the sample gas 50X in the gas cell 10X to be reflected by the modulation mirror 70X, and the reflected light enters the light receiving unit 30X.

Meanwhile, when the modulation mirror 70X is controlled in a state in which the light passes therethrough, along the optical path B1 shown by an arrow in FIG. 2, the light emitted from the infrared light source 20X passes through the sample gas 50X in the gas cell 10X to be transmitted the modulation mirror 70X, and passes through the saturated gas chamber 40X to be reflected by the reflecting mirror 60X. The light reflected by the reflecting mirror 60X passes through the saturated gas chamber 40X again to be transmitted through the modulation mirror 70X to enter the light receiving unit 30X.

As described above, when the modulation mirror 70X is controlled to be in the transmissive state, in comparison with the case in which the modulation mirror 70X is controlled to be in the reflective state, the optical path length is increased by an extent that the light passes through the saturated gas chamber 40X. In addition, as the infrared beam passes through the saturated gas 41X hermetically enclosed in the saturated gas chamber 40X, energy of the light is absorbed by the saturated gas. Accordingly, when the light receiving unit 30X receives the light passing through the saturated gas chamber 40X (when the light is transmitted through the modulation mirror 70X), in comparison with the case in which the light not passing through the saturated gas chamber 40X is received (when the light is reflected by the modulation mirror 70X), the received light energy value is decreased.

As described above, in the second embodiment, variation in received light energy values is electrically performed by the modulation mirror 70X. For this reason, since the modulation mirror is compact and further a movable part can be removed, bad effects such as a position difference, additional noise, or the like due to the vibrations are removed, and accuracy is improved. Further, a modulation speed is largely increased in comparison with a mechanical type.

(Concentration Calculation Processing of Carbon Dioxide)

In processing of calculating the concentration of the carbon dioxide using the calculation circuit 3X from the energy value of the light received by the light receiving unit 30X, similar to the case of the first embodiment, the concentration can be calculated using a gas correlation method, which is well known in the related art, and thus, detailed description thereof will not be repeated.

(Operations and Effects of Second Embodiment)

Next, operations and effects of the gas concentration calculating device 1XA according to the second embodiment will be described. According to the gas concentration calculating device 1XA of the second embodiment, since the light receiving unit 30X receives both of the light reflected by the modulation mirror 70X and the light transmitted through the modulation mirror 70X and passing through the saturated gas chamber 40X, inconvenience due to the individual differences of the light receiving unit 30X when the lights are separately received by the different light receiving units 30X, respectively, when the reflection and the transmission are switched by the modulation mirror 70X, is prevented. In addition, since the modulation mirror 70X is disposed at the other end of the gas cell 10X in which the sample gas 50X is introduced, i.e., since the modulation mirror 70X is disposed outside the gas cell 10X, even when the reflection and the transmission of the light is switched by the modulation mirror 70X, there is no variation in optical path length of the light passing through the sample gas 50X. For this reason, inconvenience due to instability of the optical path length of the light passing through the sample gas 50X can be prevented.

In addition, in the second embodiment, a means for generating variation in optical path length and a difference in received light energy values of the lights received by the light receiving unit 30X is the modulation mirror 70X, and an operation of the modulation mirror 70X is performed by electrical control of the reflectance. Accordingly, since there is no vibration or the like to generate a difference in optical path length or a difference in received light energy values and thus no position difference, additional noise, or the like due to the vibration, a decrease in optical detection accuracy of the gas concentration measuring module 2XA can be prevented.

In addition, as the modulation mirror 70X electrically controls the reflectance, the reflectance switching can be rapidly performed. Accordingly, the time deviation in the optical measurement timing of the light received by the light receiving unit 30X is negligible or remarkably short, and thus, pseudo-simultaneous measurement can be performed.

Further, as the modulation mirror 70X having such effects, a spatial light modulator (SLM) or a liquid crystal optical element is preferable.

Furthermore, using variation in characteristics when the light emitted from the infrared light source 20X passes through the same kind of saturated gas 41X as the sample gas 50X, a difference in received light energy values can be generated by the light receiving unit 30X.

[Third Embodiment]

In a third embodiment, the light emitted from the infrared light source 20X is reflected or transmitted by a rotating mirror 80X. In addition, like elements in the first embodiment are designated like reference numerals, and detailed description thereof will not be repeated.

(Overall Configuration of Gas Concentration Calculating Device 1XB)

Figure 3:
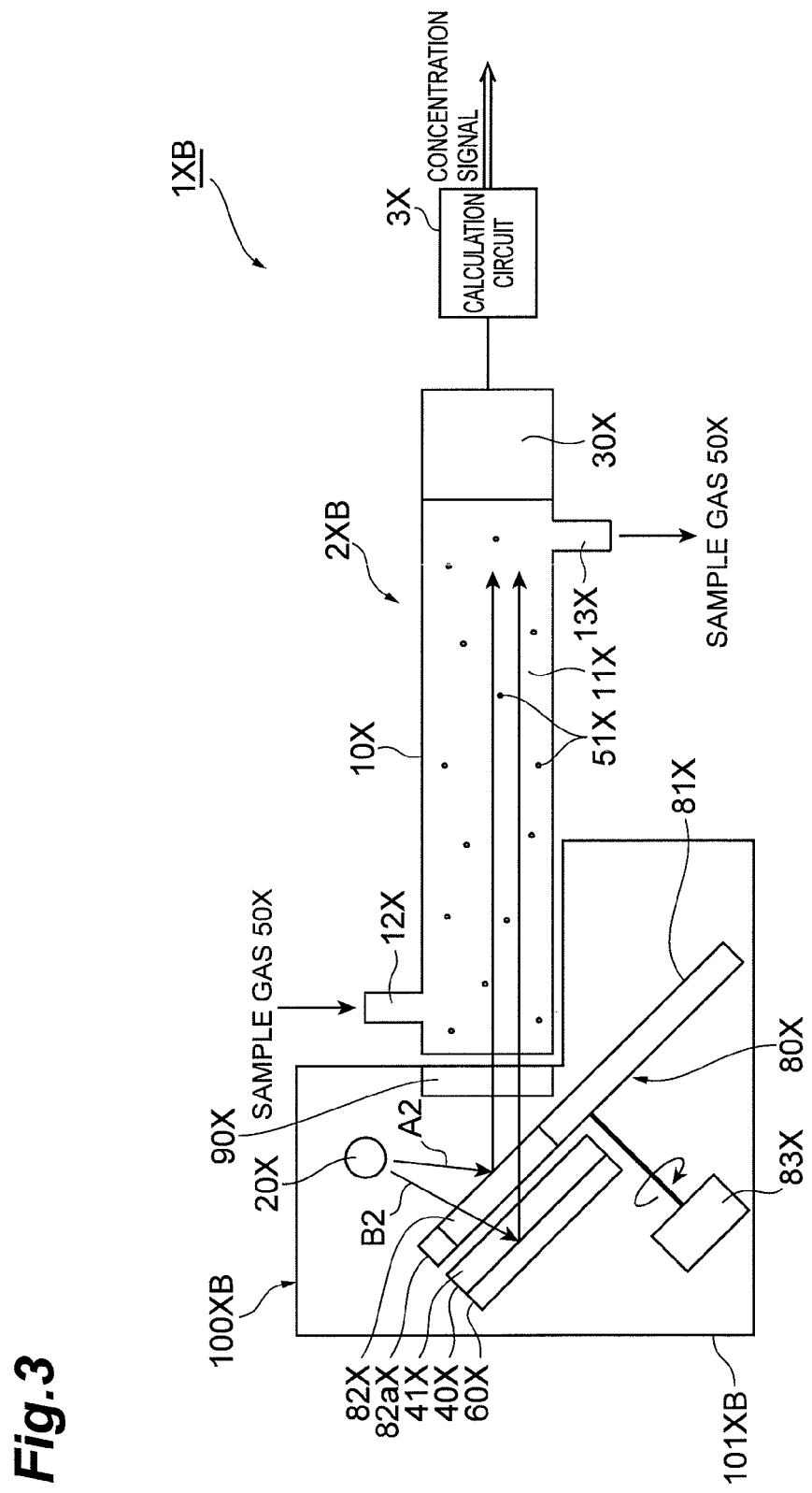
FIG. 3 is a schematic cross-sectional view of a gas concentration calculating device 1XB according to a third embodiment.

First, an overall configuration of the gas concentration calculating device 1XB according to a third embodiment will be described. FIG. 3 is a schematic cross-sectional view showing the gas concentration calculating device 1XB. The gas concentration calculating device 1XB includes a gas concentration measuring module 2XB configured to receive the light from the infrared light source 20X (corresponding to "a light source" of the claims) to measure an energy value thereof, and a calculation circuit 3X (corresponding to "a gas concentration calculating module" of the claims) configured to calculate a gas concentration based on a measurement result by the gas concentration measuring module 2XB, calculating a concentration of a target gas. The gas concentration calculated by the calculation circuit 3X is output to a control device (not shown) to be used to control, for example, an air-conditioning system, and so on. In addition, in the third embodiment, an example of the case in which carbon dioxide in the sample gas 50X introduced into the gas concentration measuring module 2XB is provided as a target gas for concentration calculation will be described.

The gas concentration measuring module 2XB includes a gas cell 10X, a reflection switching unit 100XB having the infrared light source 20X, and a light receiving unit 30X (corresponding to "a light receiving means" of the claims).

The gas cell 10X is configured to form an introduction space 11X into which the sample gas 50X is introduced. The gas cell 10X has a gas introduction unit 12X installed at one end side of the gas cell 10X and configured to introduce the sample gas 50X into the introduction space 11X, and a gas discharge unit 13X installed at the other end side of the gas cell 10X and configured to discharge the sample gas 50X in the introduction space 11X to the outside.

The reflection switching unit 100XB is disposed at one end of the gas cell 10X, and includes an infrared light source 20X, a rotating mirror 80X (corresponding to "a reflection switching means, a rotary mechanism" of the claims), a saturated gas chamber 40X (corresponding to "a comparison gas cell" of the claims) in which the saturated gas 41X (corresponding to "a comparison gas" of the claims) is hermetically sealed, a reflecting mirror 60X (corresponding to "a reflecting means" of the claims), and a band pass filter 90X.

The infrared light source 20X is configured to emit infrared rays. In the third embodiment, a light source configured to emit light having a wavelength range of 4.2 µm to 4.3 µm is used as the infrared light source 20X. The infrared rays from the infrared light source 20X are absorbed and attenuated by the carbon dioxide molecules 51X in the sample gas 50X.

The rotating mirror 80X is rotated to reflect or transmit the light emitted from the infrared light source 20X. The rotating mirror 80X is constituted by a reflecting plate 81X and a hole 82X, and a rotational direction, a rotational speed, or the like thereof is controlled by a rotation driving mechanism 83X. The hole 82X is a space surrounded by a frame 82aX.

The reflecting mirror 60X is configured to reflect the light passing through the hole 82X of the rotating mirror 80X toward the light receiving unit 30X. Here, the saturated gas chamber 40X is disposed between the reflecting plate 81X of the rotating mirror 80X and the reflecting mirror 60X. For this reason, the light passing through the hole 82X of the rotating mirror 80X passes through the saturated gas 41X in the saturated gas chamber 40X to be reflected by the reflecting mirror 60X. The light reflected by the reflecting mirror 60X passes through the saturated gas 41X again to pass through the hole 82X of the rotating mirror 80X, entering the light receiving unit 30X. In addition, FIG. 3 shows a state in which the light emitted from the infrared light source 20X passes through the hole 82X of the rotating mirror 80X to be reflected by the reflecting mirror 60X.

The same kind of saturated gas as the sample gas 50X is used as the saturated gas 41X hermetically enclosed in the saturated gas chamber 40X.

The band pass filter 90X is disposed on an optical path between the infrared light source 20X and the light receiving unit 30X, and allows transmission of the light having a predetermined wavelength only. In the third embodiment, the band pass filter 90X is disposed in the reflection switching unit 100XB, and used to allow transmission of the light having a wavelength range of 4.2 µm to 4.3 µm only. In addition, when the band pass filter 90X is not installed in the reflection switching unit 100XB, for example, the band pass filter 90X may be installed between the light receiving unit 30X and the gas cell 10X.

In addition, for example, an inert gas, which is inert with respect to the infrared ray emitted from the infrared light source 20X, or the sample gas 50X is filled in the housing 101XB of the reflection switching unit 100XB.

The light receiving unit 30X is a light receiving element disposed at the other end of the gas cell 10X and configured to receive both of the light emitted from the infrared light source 20X and reflected by the reflecting plate 81X of the rotating mirror 80X and the light emitted from the infrared light source 20X and passing through the hole 82X of the rotating mirror 80X to pass through the saturated gas chamber 40X. That is, one light receiving unit 30X receives both of the light passing through the saturated gas chamber 40X and the light not passing through the saturated gas chamber 40X. Accordingly, in comparison with the case in which a plurality of light receiving means are used to receive a plurality of kinds of lights, respectively, there is no bad effect due to individual differences of the light receiving means.

(Structure for Generating Difference in Received Light Energy Values)

A difference in received light energy values of the lights received by the light receiving unit 30X will be described. Here, as reflection of the light from the reflecting plate 81X or transmission of the light through the hole 82X by rotation of the rotating mirror 80X are controlled, the difference in received light energy values of the lights received by the light receiving unit 30X can be generated.

Specifically, as the reflecting plate 81X is rotated, when the rotating mirror 80X is controlled in a state in which the light is reflected by the reflecting plate 81X, along the optical path A2 shown by an arrow in FIG. 3, the light emitted from the infrared light source 20X is reflected by the reflecting plate 81X of the rotating mirror 80X, and the reflected light passes through the sample gas 50X in the gas cell 10X to enter the light receiving unit 30X.

Meanwhile, when the rotating mirror 80X is controlled in a state in which the light passes through the hole 82X, along the optical path B2 shown by an arrow in FIG. 3, the light emitted from the infrared light source 20X passes through the hole 82X of the rotating mirror 80X to pass through the saturated gas chamber 40X to be reflected by the reflecting mirror 60X. The light reflected by the reflecting mirror 60X passes through the saturated gas chamber 40X again to pass through the hole 82X of the rotating mirror 80X, and further enters the light receiving unit 30X through the sample gas 50X in the gas cell 10X.

As described above, when the rotating mirror 80X is controlled in a state in which the light passes through the hole 82X, in comparison with the case in which the control is performed in a state in which the light is reflected by the reflecting plate 81X, the optical path length is increased by an extent that the light passes through the saturated gas chamber 40X. In addition, as the infrared beam passes through the saturated gas 41X hermetically enclosed in the saturated gas chamber 40X, the energy of the light is absorbed by the saturated gas. Accordingly, when the light receiving unit 30X receives the light passing through the saturated gas chamber 40X (when the light passes through the hole 82X), in comparison with the case in which the light not passing through the saturated gas chamber 40X is received (when the light is reflected by the reflecting plate 81X), the received light energy value is reduced.

As described above, in the third embodiment, variation in received light energy values is performed by rotation of the rotating mirror 80X. Since the rotating mirror 80X is disposed at one end of the gas cell 10X into which the sample gas 50X is introduced, even when the rotating mirror 80X is rotated, there is no variation in optical path lengths that the light reflected by the reflecting plate 81X and the light passing through the hole 82X pass through the target gas. Accordingly, since the optical path length is stable, even when the rotating mirror 80X is not temporarily stopped, the measurement with high accuracy can be realized. As a result, generation of the large time deviation in the measurement timing of the light due to temporary movement stoppage of the rotating mirror 80X can be prevented.

(Concentration Calculation Processing of Carbon Dioxide)

Next, processing of calculating a concentration of the carbon dioxide using the calculation circuit 3X from the energy values of the lights received by the light receiving unit 30X will be described. The light receiving unit 30X outputs the received light energy value of the light reflected by the reflecting plate 81X of the rotating mirror 80X and passing through the sample gas 50X only and the received light energy value of the light transmitted through the hole 82X of the rotating mirror 80X and passing through the saturated gas chamber 40X and the sample gas 50X to the calculation circuit 3X. The calculation circuit 3X can calculate the concentration of the carbon dioxide in the sample gas 50X by calculating an increase or decrease in an emitted amount based on the received light energy value of the light passing through the saturated gas chamber 40X and the sample gas 50X and correcting the received light energy value of the light passing through the sample gas 50X only. In addition, in a sequence of calculating the gas concentration based on the two received light energy values, for example, as disclosed in Patent Document 1, the calculation can be performed using a gas correlation method, which is well-known in the related art, and detailed description thereof will be omitted.

(Operations and Effects of Third Embodiment)

Next, operations and effects of the gas concentration calculating device 1XB according to the third embodiment will be described. According to the gas concentration calculating device 1XB of the third embodiment, since the light receiving unit 30X receives both of the light reflected by the reflecting plate 81X of the rotating mirror 80X and the light passing through the hole 82X of the rotating mirror 80X and passing through the saturated gas chamber 40X, inconvenience due to the individual differences of the light receiving unit 30X when the lights are separately received by the different light receiving units 30X, respectively, when the reflection and transmission are switched by the modulation mirror 80X is prevented. In addition, since the rotating mirror 80X is disposed at one end of the gas cell 10X into which the sample gas 50X is introduced, i.e., since the rotating mirror 80X is disposed outside the gas cell 10X, even when the reflection and transmission of the light are switched by the rotating mirror 80X, there is no variation in optical path length of the light passing through the sample gas 50X. For this reason, inconvenience due to instability of the optical path length of the light passing through the sample gas 50X can be prevented.

In addition, for example, unlike Patent Document 2, since the optical path length is stable, there is no need to temporarily stop the rotating mirror 80X. As a result, inconvenience such as generation of the large time deviation in the measurement timing of the light due to temporary movement stoppage of the rotating mirror 80X can be prevented.

Further, since the rotating mirror 80X is constituted by the reflecting plate 81X and the hole 82X, the rotating mirror 80X has a simple structure. In this case, since a rotating portion is formed of a thin disc, a drive power for rotating the reflecting plate 81X may be low, and thus, the rotating mirror 80X can be minimized.

In addition, one aspect of the present invention is not limited to the respective embodiments.

Figure 4:
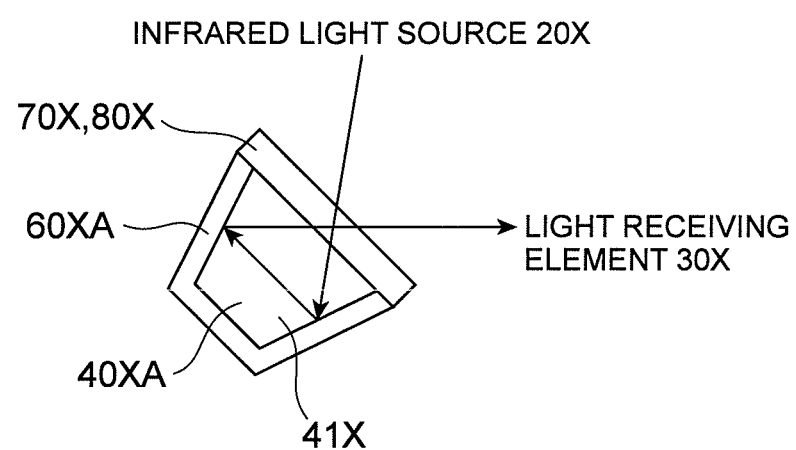
FIG. 4 is a view showing a variant of a reflecting mirror 60X.

For example, instead of the configuration in which the reflecting mirror 60X is disposed at a rear stage of the modulation mirror 70X or the rotating mirror 80X as shown in FIGS. 1 to 3, the reflecting mirror 60XA can be formed at a circumferential surface of the saturated gas chamber 40XA using a conical saturated gas chamber 40XA, as shown in FIG. 4. In this case, the light emitted from 21 and passing through the modulation mirror 70X or the rotating mirror 80X is sequentially reflected by the inside of the reflecting mirror 60XA, and passes through the saturated gas chamber 40XA for each reflection. Accordingly, the optical path length passing through the saturated gas chamber 40XA can be increased, and the energy of the light emitted from the infrared light source 20X can be sufficiently absorbed by the saturated gas 41X of the saturated gas chamber 40X. In addition, since the configuration in which the light passes through the comparison gas cell a plurality of times is provided, the optical path length of the light passing through the comparison gas cell can be increased by a compact comparison gas cell, rather than a large-sized comparison gas cell.

In addition, in FIG. 4, while the light is reflected by the conical reflecting mirror 60XA a plurality of times, the shape is not limited thereto but, for example, a triangular pyramidal shape or a pyramidal shape having a plurality of reflecting surfaces may be provided. In addition, "a plurality of reflecting surfaces having different angles" in the claims includes the case in which the reflecting surface is curved when the reflecting mirror 60XA has a conical shape.

Further, the saturated gas chamber 40X and the band pass filter 90X can have a removable configuration. In this case, as the saturated gas chamber 40X is prepared in a plural number in which different saturated gases 41X are hermetically enclosed, or the band pass filter 90X is prepared in a plural number through which lights of different wavelengths pass, according to the sample gas 50X introduced into the gas cell 10X or the kind of gas to be measured, optimal ones from the saturated gas chambers 40X or the band pass filters 90X can be selected and used to measure concentrations of various kinds of gases.

In addition, the plurality of gas cells 10X and light receiving units 30X are provided with respect to one modulation mirror 70X or one rotating mirror 80X, and different kinds of gases can be introduced into the gas cells 10X. In this case, the plurality of kinds of gas concentrations can be simultaneously measured.

Figure 5:
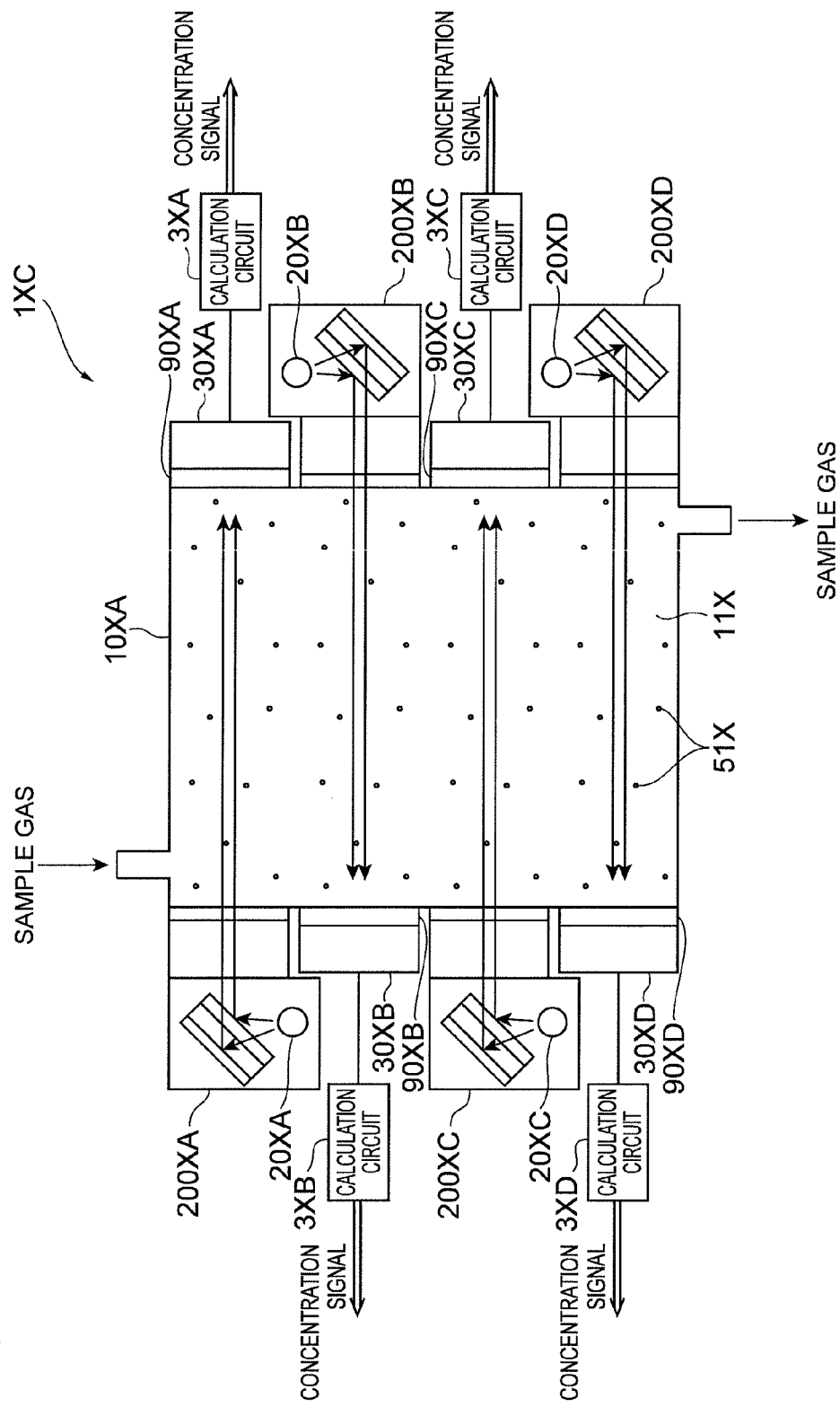
FIG. 5 is a schematic cross-sectional view according to a variant of the gas concentration calculating device 1X.

Next, a variant of the gas concentration calculating device for detecting a gas concentration of a sample gas in which a plurality of kinds of gases are mixed is shown. Each of gas concentrations should be measured by using comparison gas chambers in which a gas intended to be measured is provided as a saturated gas and the lights having different wavelengths to calculate concentrations of the plurality of different kinds of gases as mentioned above. In order to realize the measurement, in the gas concentration measuring module of the variant, a gas concentration calculating module is provided at each light receiving means using a plurality of sets of reflection switching units and light receiving means. FIG. 5 is a schematic cross-sectional view showing a gas concentration calculating device 1XC for measuring a gas concentration of each gas in the sample gas in which 4 kinds of gases are mixed. Since reflection switching units 200XA to 200XD are increased in volume in comparison with light receiving units 30XA to 30XD, in both ends of a gas cell 10XA, the reflection switching unit 200XA is disposed at a left side and the light receiving unit 30XA is disposed at a right side of the uppermost stage in FIG. 5, the light receiving unit 30XB is disposed at a left side and the reflection switching unit 200XB is disposed at a right side of the next stage, the reflection switching unit 200XC is disposed at a left side and the light receiving unit 30XC is disposed at a right side of the next stage, and the light receiving unit 30XD is disposed at a left side and the reflection switching unit 200XD is disposed at a right side of the next stage. Accordingly, even when a set of each of the reflection switching units and each of the light receiving units uses the common gas cell 10XA, the gas concentration calculating device 1XC is entirely reduced in size.

Light sources 20XA to 20XD configured to emit lights having wavelengths to be used in the measurement are disposed at the reflection switching units 200XA to 200XD disposed outside the gas cell 10XA, respectively. In addition, when the emitted light has a wide wavelength region and includes a wavelength range that can be used to absorb each gas, one light source can be used. Each of the reflection switching units 200XA to 200XD has the same configuration as the reflection switching unit 100X of the above-mentioned first embodiment, and the saturated gas corresponding to a gas to be measured is hermetically enclosed in the comparison gas chamber in each of the reflection switching units 200XA to 200XD. The lights emitted from the light sources 20XA to 20XD of the reflection switching units 200XA to 200XD are reflected by reflecting mirrors or modulation mirrors installed at the reflection switching units 200XA to 200D to enter the light receiving units 30XA to 30XD, respectively.

In addition, the band pass filters 90XA to 90XD are disposed at the light receiving units 30XA to 30XD, respectively. Each of the band pass filters 90XA to 90XD is optical element configured to transmit the light having wavelength absorbed by the gas, which is to be measured at each of the light receiving units 30XA to 30XD and block the lights having other wavelengths. The band pass filters 90XA to 90XD are different at the light receiving units 30XA to 30XD, respectively. Based on the energy values of the lights received by the light receiving units 30XA to 30XD, the calculation circuits 3XA to 3XD calculate concentration of the gases to be measured.

Figure 6:
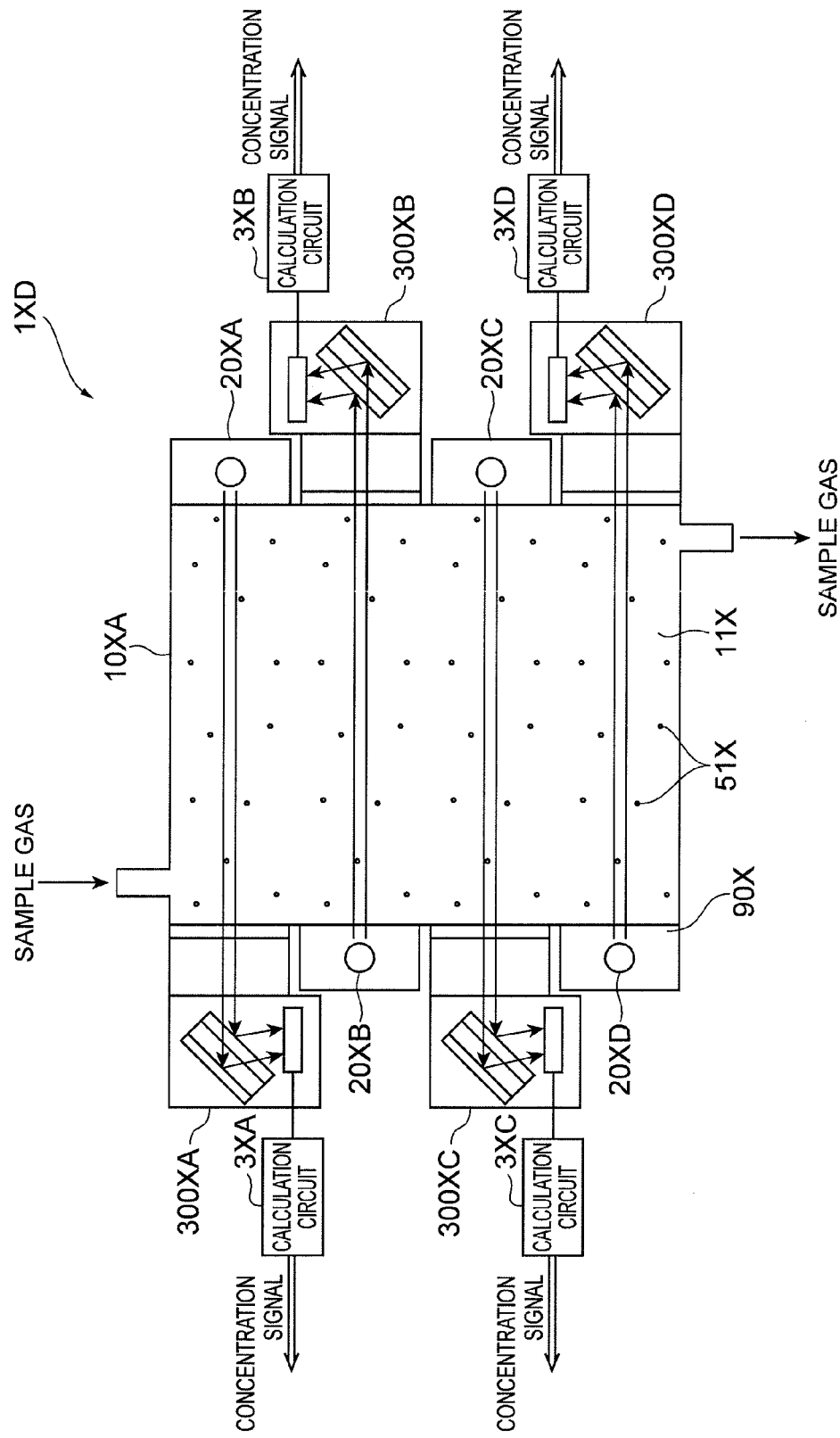
FIG. 6 is a schematic cross-sectional view according to a variant of the gas concentration calculating device 1X.

In the above-mentioned variant, while the reflection switching units 200XA to 200XD and the light receiving units 30XA to 30XD are alternately disposed, similar to the gas concentration calculating device 1XD shown in FIG. 6, the light sources 20XA to 20XD and reflection switching units 300XA to 300XD including light receiving units configured to respectively receive lights emitted from the light sources 20XA to 20XD may be alternately disposed at both ends of the gas cell 10XA.

Figure 7:
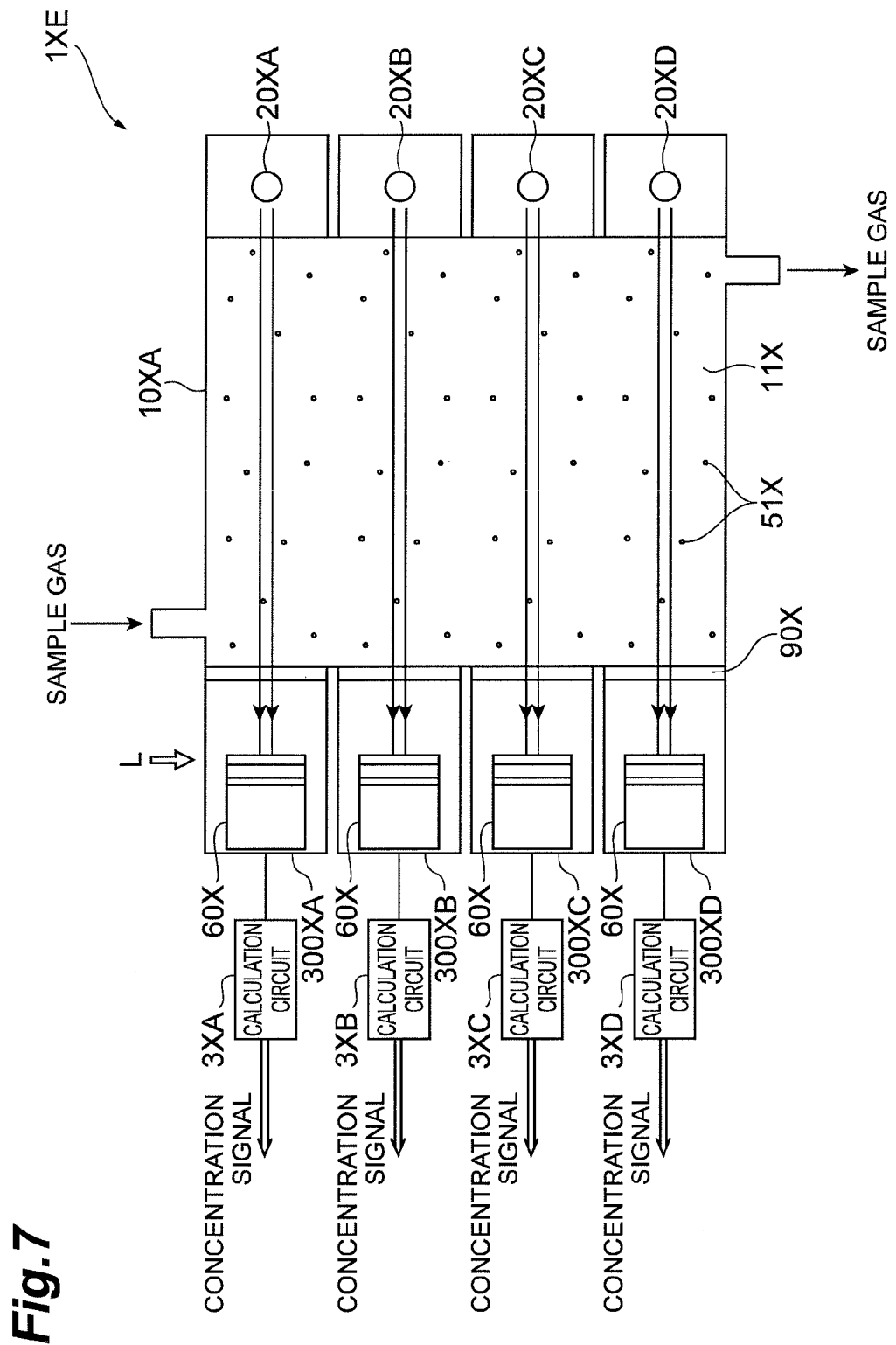
FIG. 7 is a schematic cross-sectional view according to a variant of the gas concentration calculating device 1X.
Figure 8:
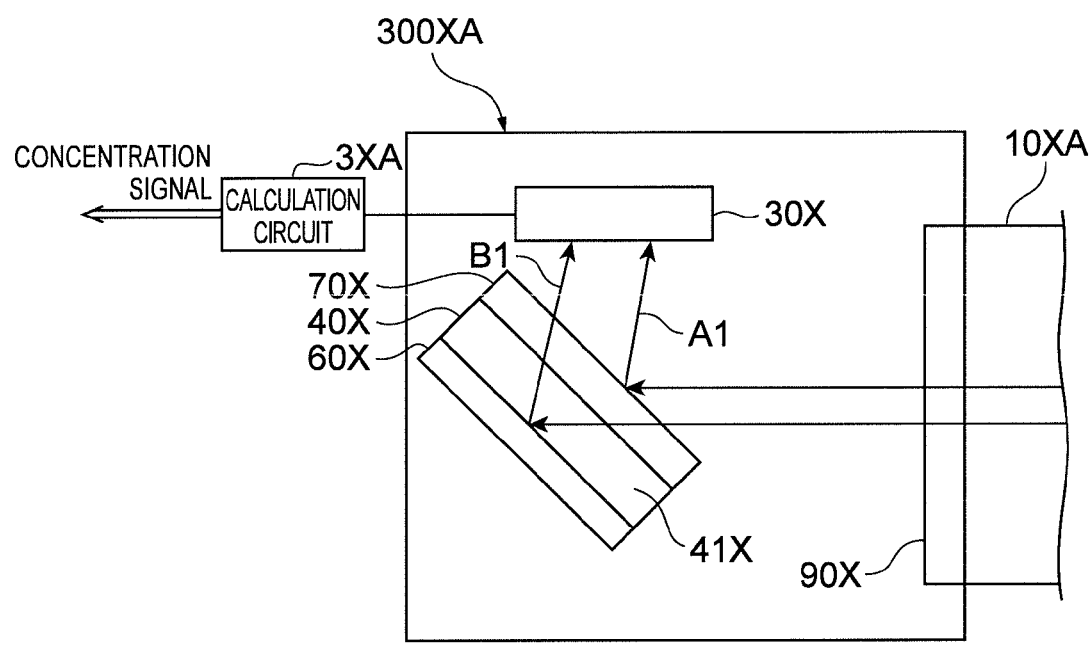
FIG. 8 is a view showing a direction of a reflection switching unit 300XA of FIG. 7 when seen from a direction of an arrow L.

In addition, FIG. 7 shows a gas concentration calculating device 1XE according to another variant. FIG. 8 is a view showing the reflection switching unit 300XA of the gas concentration calculating device 1XE when seen in a direction of the arrow L in FIG. 7. As shown in FIG. 7, in the gas concentration calculating device 1XE according to the variant, the reflection switching units 300XA to 300XD are disposed at one side of the gas cell 10XA and the light sources 20XA to 20XD are aligned with the other side. The reflection switching units 300XA to 300XD have the same configuration as the reflection switching unit 100XA of the second embodiment described with reference to FIG. 2. The reflection switching units 300XA to 300XD reflect the lights emitted from the light sources 20XA to 20XD in a direction perpendicular to an alignment direction of the reflection units 300XA to 300XD using the reflecting mirrors and the modulation mirrors to receive the lights using the light receiving units, respectively. That is, the lights emitted from the light sources 20XA to 20XD are reflected in an inward direction of FIG. 7 by the reflecting mirrors and the modulation mirrors to be received by the light receiving unit 30X. In addition, in the case of the gas concentration calculating device 1XE shown in FIGS. 7 and 8, when the light source emits the lights having wavelengths used to measure the plurality of gases, only one light source may be provided, rather than preparing the light sources 20XA to 20XD for the respective gases.

In addition, the concentrations of the gases calculated by the gas concentration calculating devices 1X, 1XA to 1XE can be applied to various instruments for calculating a concentration of a gas, in addition to control of air-conditioning.

[Fourth Embodiment]

(Overall Configuration of Gas Concentration Calculating Device 1Y)

Figure 9:
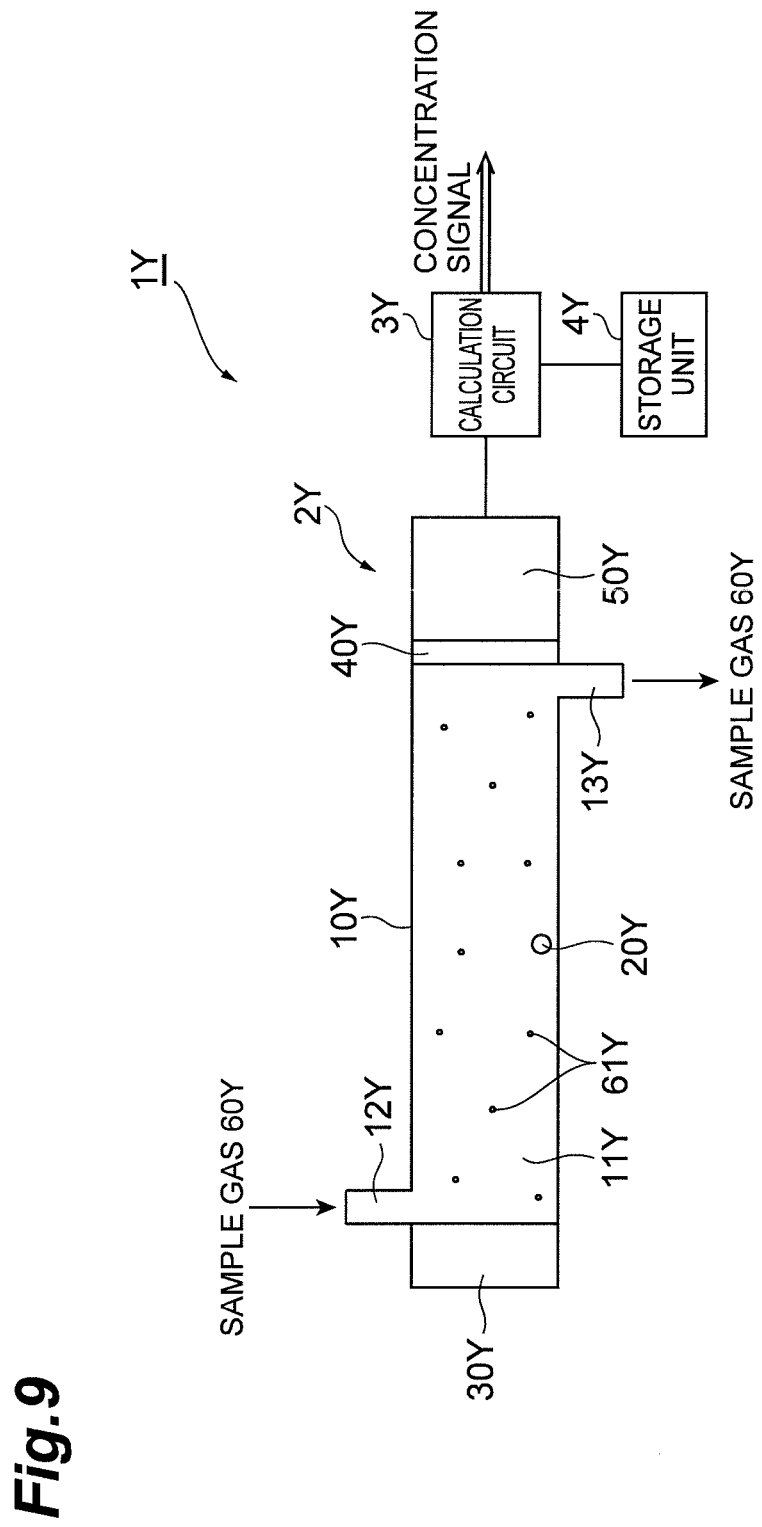
FIG. 9 is a schematic cross-sectional view showing a gas concentration calculating device 1Y.

First, an overall configuration of the gas concentration calculating device 1Y according to a fourth embodiment will be described. FIG. 9 is a schematic cross-sectional view showing the gas concentration calculating device 1Y. The gas concentration calculating device 1Y includes a gas concentration measuring module 2Y configured to receive light from a light source 20Y to measure an energy value thereof, a calculation circuit 3Y (corresponding to "a gas concentration calculating module" of the claims) configured to calculate a gas concentration based on a measurement result by the gas concentration measuring module 2Y, and a storage unit 4Y (corresponding to "a storage means" of the claims) configured to store necessary information when the calculation circuit 3Y calculates the gas concentration, calculating a concentration of a target gas. The gas concentration calculated by the calculation circuit 3Y is output to a control device (not shown) to be used to control, for example, an air-conditioning system, and so on. In addition, in the fourth embodiment, the case in which carbon dioxide in a sample gas 60Y introduced into the gas concentration measuring module 2Y is provided as a target gas for concentration calculation will be described.

The gas concentration measuring module 2Y includes a gas cell 10Y, the light source 20Y, a modulation mirror 30Y (corresponding to "a reflectance modulation means" of the claims), a band pass filter 40Y, and a light receiving unit 50Y (corresponding to "a light receiving means" of the claims).

The gas cell 10Y forms an introduction space 11Y into which the sample gas 60Y is introduced. The gas cell 10Y has a gas introduction unit 12Y installed at one end side of the gas cell 10Y and configured to introduce the sample gas 60Y into the introduction space 11Y, and a gas discharge unit 13Y installed at the other end side of the gas cell 10Y and configured to discharge the sample gas 60Y in the introduction space 11Y to the outside. The gas discharge unit 13Y may be a plurality of holes formed in an inner wall (for example, a bottom portion) of the gas cell.

The light source 20Y is disposed in the gas cell 10Y and configured to emit infrared rays. In the fourth embodiment, a light source configured to emit light including light having a wavelength range of 4.2 µm to 4.3 µm is used as the light source 20Y. In FIG. 9, while an example in which the light source 20Y is disposed at the bottom portion of a center in the gas cell 10Y is shown, the light source 20Y is not limited thereto but may be disposed at a top portion or a center portion of the center in the gas cell 10Y or may be disposed at the modulation mirror 30Y side or the light receiving unit 50Y side in a somewhat offset manner. The infrared rays from the light source 20Y are absorbed and attenuated by carbon dioxide molecules 61Y in the sample gas 60Y.

The modulation mirror 30Y is disposed at one end of the gas cell 10Y and configured to electrically modulate a reflectance with respect to the light emitted from the light source 20Y. In the fourth embodiment, for example, a liquid crystal optical element, or an electro-optic device (EO device) is employed as the modulation mirror 30Y. In addition to this, another technique may be used to perform control of the reflectance at a dielectric substance, a metal mesh, or the like.

The band pass filter 40Y is disposed on an optical path between the light source 20Y and the light receiving unit 50Y to allow transmission of the light having a predetermined wavelength only. In the fourth embodiment, the band pass filter 40Y is disposed at an end of the light receiving unit 50Y side of the gas cell 10Y to allow transmission of the light having a wavelength range of 4.2 µm to 4.3 µm only.

The light receiving unit 50Y is a light receiving element disposed at the other end of the gas cell 10Y and configured to receive both of a direct light directly emitted from the light source 20Y and a reflection light emitted from the light source 20Y and reflected by the modulation mirror 30Y. That is, one light receiving unit 50Y receives both of the direct light and the reflection light. In other words, one light receiving unit 50Y receives the lights when the reflectance is electrically modified by the modulation mirror 30Y (as described below, a direct light, a sum of a direct light and a reflection light, and so on). Accordingly, in comparison with the case in which the plurality of light receiving means are used to receive a plurality of kinds of lights, respectively, there is no bad effect due to individual differences of the light receiving means.

(Structure for Generating Difference in Optical Path Length or Received Light Energy Value)

FIG. 10 is a view for describing a structure for generating a difference in an optical path length or a received light energy value in the fourth embodiment. Similar to FIG. 9, variations in the optical path length and the received light energy value of the light emitted from the light source 20Y disposed at the center portion of the gas cell 10Y and arriving at the light receiving unit 50Y is performed by variation in reflectance of the modulation mirror 30Y. In the description, for the convenience of description, it is assumed that the modulation mirror 30Y performs total reflection (the modulation mirror 30Y is ON) or total transmission (the modulation mirror 30Y is OFF) to modify the reflectance.

FIG. 10(A) shows a situation in which the light arriving from the light source 20Y is totally reflected in a state in which the modulation mirror 30Y is ON. In FIG. 10(A), the direct light emitted from the light source 20Y and directly arriving at the light receiving unit 50Y is designated by l1 (→), and a length of the optical path through which the direct light passes is about L. In addition, the reflection light is designated by l1 (←) (the light emitted from the light source 20Y and arriving at the modulation mirror 30Y) and l2 (the light reflected by the modulation mirror 30Y and arriving at the light receiving unit 50Y), and a length of the optical path through which the reflection light passes is about 3L (L+2L). In the state in which the modulation mirror 30Y is ON, both of the direct light and the reflection light arrive at the light receiving unit 50Y via the optical paths of L and 3L respectively, and the received light energy values are measured. Meanwhile, FIG. 10(B) shows a situation in which the light arriving from the light source 20Y passes through the modulation mirror 30Y, without being reflected at all, in a state in which the modulation mirror 30Y is OFF. In this case, only the direct light arrives at the light receiving unit 50Y via the optical path of about L, and the received light energy value is measured. In addition, in FIG. 10, ON/OFF of the modulation mirror 30Y are designated by presence and absence of hatching. Further, in FIG. 10(B), while transmission of the non-reflected light is shown, the light is not limited thereto but may be absorbed.

As described above, in the fourth embodiment, variations in the optical path length and the received light energy value are electrically performed by the modulation mirror 30Y. For this reason, since the modulation mirror is compact and further a movable part can be removed, bad effects such as a position difference, additional noise, or the like due to the vibrations are removed, and accuracy is improved. Further, a modulation speed is largely increased in comparison with a mechanical type.

(Stored Information of Storage Unit 4Y)

Next, information stored in the storage unit 4Y will be described. A database or an approximate equation representing a correlation between a ratio of the received light energy values of the light receiving unit 50Y and a concentration of carbon dioxide, which is a target gas, in each case in which the reflectance is electrically modified by the modulation mirror 30Y, is previously stored in the storage unit 4Y.

Figure 11:
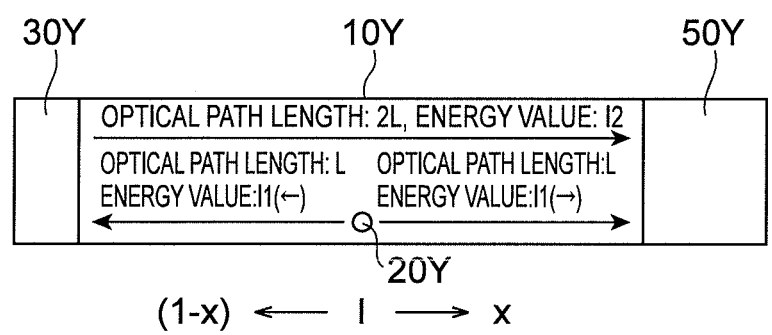
FIG. 11 is a view for describing stored information of a storage unit 4Y.

FIG. 11 is a view for describing the stored information of the storage unit 4Y. While FIG. 11 is basically similar to FIG. 9 or 10, only elements needed for the following description remain, and the optical path lengths are schematically shown by L or 2L. In FIG. 11, the following Equations (1) to (3) are satisfied.

$$I = I1(\rightarrow) + I1(\leftarrow) \quad (1)$$

$$I1(\rightarrow)/I = x \quad (2)$$

$$I1(\leftarrow)/I = 1 - x \quad (3)$$

Here, I is a total energy value of infrared rays emitted from the light source 20Y, I1 ($\rightarrow$) is an energy value of the infrared rays emitted from the light source 20Y in a rightward direction in FIG. 11 as a direct light, I1 ($\leftarrow$) is an energy value of the infrared rays emitted from the light source 20Y in a leftward direction in FIG. 11, and x is a distribution ratio between I1 ($\rightarrow$) and I1 ($\leftarrow$).

In FIG. 11, when the modulation mirror 30Y is in an ON state, according to Lambert-Beer's Law, the following Equations (4) to (7) are satisfied.

$$I1(\rightarrow) = xI\exp(-KCL) \quad (4)$$

$$I1(\leftarrow) = (1-x)I\exp(-KCL) \quad (5)$$

$$I2 = (I1(\leftarrow)Ron)\exp(-2KCL) = (((1-x)I\exp(-KCL))Ron)\exp(-2KCL) \quad (6)$$

$$Ion = I1(\rightarrow) + I2 = xI\exp(-KCL) + (((1-x)I\exp(-KCL))Ron)\exp(-2KCL) \quad (7)$$

Here, K is an absorption coefficient, C is a concentration of carbon dioxide in the sample gas 60Y introduced into the gas cell 10Y, L is a distance from the light source 20Y to the light receiving unit 50Y, 2L is a distance from the modulation mirror 30Y to the light receiving unit 50Y, I2 is an energy value of the infrared rays, which are the reflection light, emitted from the light source 20Y in the leftward direction and reflected by the modulation mirror 30Y, Ron is a reflectance in a state in which the modulation mirror 30Y is ON, and Ion is total energy of the infrared ray arriving at the light receiving unit 50Y in a state in which the modulation mirror 30Y is ON, i.e., a total energy value of the direct light and the reflection light.

In addition, in FIG. 11, when the modulation mirror 30Y is in an OFF state, according to Lambert-Beer's Law, the following Equations (8) to (11) are satisfied.

$$I1(\rightarrow) = xI\exp(-KCL) \quad (8)$$

$$I1(\leftarrow) = (1-x)I\exp(-KCL) \quad (9)$$

$$I2 = (I1(\leftarrow)Roff)\exp(-2KCL) = (((1-x)I\exp(-KCL))Roff)\exp(-2KCL) \quad (10)$$

$$Ioff = I1(\rightarrow) + I2 = xI\exp(-KCL) + (((1-x)I\exp(-KCL))Roff)\exp(-2KCL) \quad (11)$$

Here, Roff is a reflectance in a state in which the modulation mirror 30Y is OFF, and Ioff is total energy of the infrared rays arriving at the light receiving unit 50Y in a state in which the modulation mirror 30Y is OFF, i.e., a total energy value of the direct light and the reflection light.

A ratio between the energy value Ion of the light received by the light receiving unit 50Y in a state in which the modulation mirror 30Y is ON and the energy value Ioff of the light received by the light receiving unit 50Y in a state in which the modulation mirror 30Y is OFF (corresponding to "a ratio of received light energy values of the light receiving means in each case in which a reflectance is electrically modified by a reflectance modulation means" of the claims) is as follows.

$$Ion/Ioff = [xI\exp(-KCL) + (((1-x)I\exp(-KCL))Ron)\exp(-2KCL)]/[xI\exp(-KCL) + (((1-x)I\exp(-KCL))Roff)\exp(-2KCL)] \quad (12)$$

Provisionally, when Roff=0 and x=0.5, i.e., when the modulation mirror 30Y is totally transparent (total transmission) in the OFF state and distribution of the light source 20Y is reduced to half, a ratio between Ion and Ioff satisfies the following relation.

$$Ion/Ioff = (1 + (Ron)\exp(-2KCL)) \quad (13)$$

Here, since Ron, K and L are constant according to equipment configuration, Equation (13) can be rewritten as follows.

$$C = f(\text{Ratio(transparent mirror)}) \quad (14)$$

Here, Ratio (transparent mirror) is a ratio of Ion and Ioff when Roff=0 and x=0.5, and f is a function, which is an approximate equation showing a correlation between Ratio (transparent mirror) and the concentration C. The storage unit 4Y stores information showing an approximate equation f of Equation (14).

Meanwhile, instead of obtaining the approximate equation f, using already known I, K, C, L, x, Ron and Roff and using Equation (7) or (11), Ion or Ioff in each case may be calculated, and a ratio Ion/Ioff may be calculated. Then, the result is used to draft a database as a table. FIG. 12 shows one example of the database drafted as described above. In the database of FIG. 12, concentrations of carbon dioxide corresponding to the respective values of Ion/I, Ioff/I and Ion/Ioff are shown.

Figure 13:
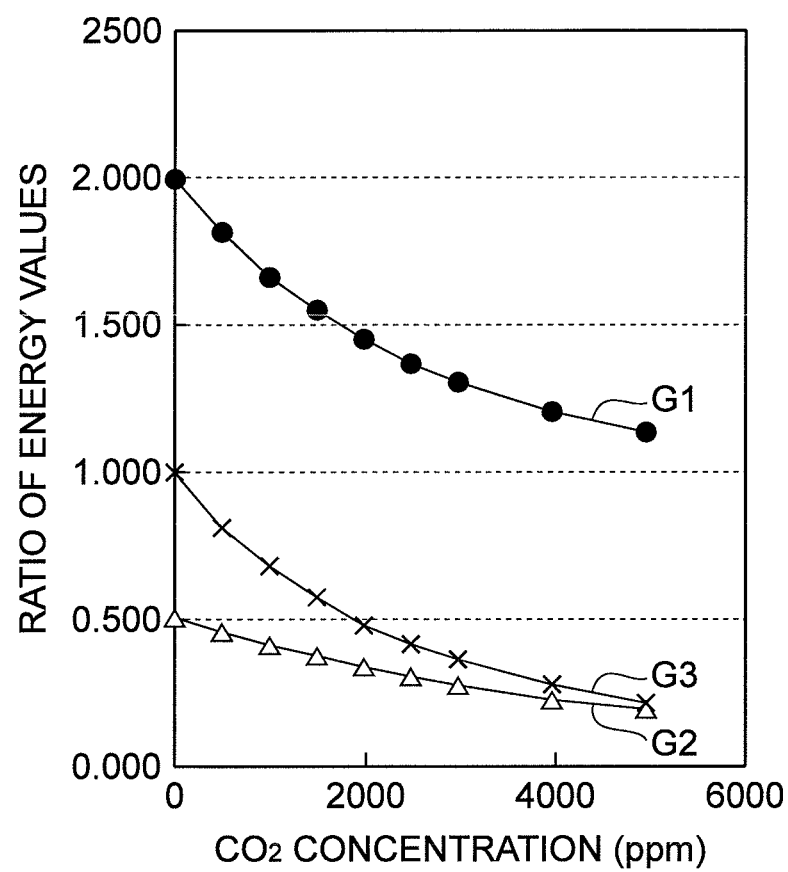
FIG. 13 is a view showing one example of a graph stored in the storage unit 4Y.

In addition, using the database of FIG. 12, a graph shown in FIG. 13 may be obtained. The graphs shown in FIG. 13 show correlations between the concentrations of carbon dioxide and the ratios Ion/Ioff. In FIG. 13, G1 is a graph showing a correlation between the concentration of carbon dioxide and the ratio Ion/Ioff, G2 is a graph showing a correlation between the concentration of carbon dioxide and the ratio Ion/I, and G3 is a graph showing a correlation between the concentration of carbon dioxide and the ratio Ioff/I. The storage unit 4Y stores information showing the above-mentioned database or graph. In addition, in FIG. 12 or 13, in order to easily understand the database or the graph, when the concentration of the carbon dioxide is zero ppm, while the graph shows that the ratio of each energy value with respect to the energy value I emitted from the light source, Ion/I becomes 1, Ioff/I becomes 0.5, and I1($\rightarrow$)/I, I1($\leftarrow$)/I and I2/I becomes 0.5, in actual measurement, since the energy I emitted from the light source cannot be measured, among the values shown in the database or the graph, the value obtained as a measurement value is only the ratio Ion/Ioff of the energy values.

As described above, based on the approximate equation f of Equation (14), the database of FIG. 12 or the graph of FIG.

13, since the correlation between the concentration of the carbon dioxide and Ion/Ioff can be known, when Ion/Ioff is measured, the concentration of the carbon dioxide can be calculated.

(Concentration Calculation Processing of Carbon Dioxide)

Figure 14:
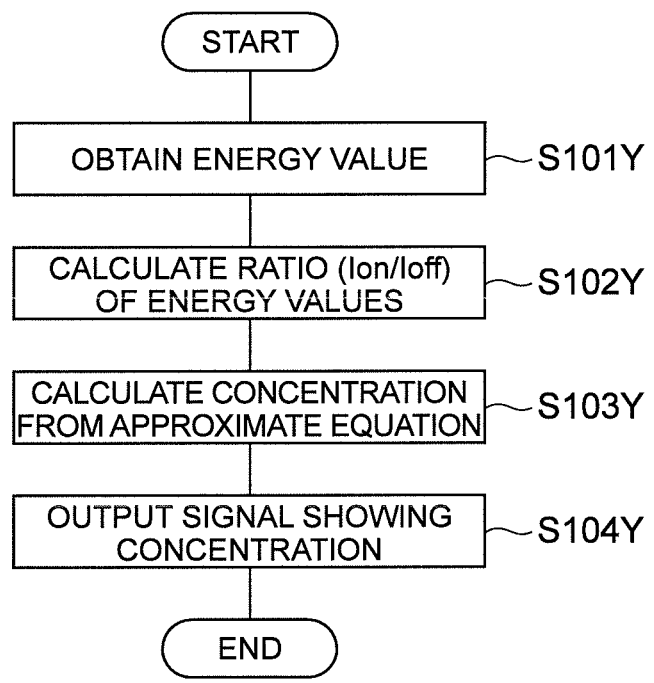
FIG. 14 is a flowchart showing a flow of carbon dioxide concentration calculation processing by a gas concentration calculating device 1Y.

Next, a flow of processing of calculating a concentration of carbon dioxide using the calculation circuit 3Y from the energy value of the light received by the light receiving unit 50Y will be described. The calculation circuit 3Y is a computation circuit configured to calculate the concentration of the carbon dioxide corresponding to the ratio based on the ratio (the Ion/Ioff) of the received light energy values of the light receiving unit 50Y and based on the above-mentioned approximate equation f, the database of FIG. 12 or the graph of FIG. 13, in each case in which the reflectance is electrically modified by the modulation mirror 30Y, and including a CPU, and so on. FIG. 14 is a flowchart showing a flow of the carbon dioxide concentration calculation processing.

In step S101Y, the calculation circuit 3Y obtains the energy value Ion of the light received by the light receiving unit 50Y in a state in which the modulation mirror 30Y is ON, and the energy value Ioff of the light received by the light receiving unit 50Y in a state in which the modulation mirror 30Y is OFF.

Next, in step S102Y, the calculation circuit 3Y calculates the ratio (Ion/Ioff) between the obtained energy value Ion and energy value Ioff. In step S103Y, the calculation circuit 3Y calculates the concentration of the carbon dioxide from the ratio (Ion/Ioff) calculated in step S103Y using the approximate equation f stored in the storage unit 4Y. As the concentration is calculated using the approximate equation f, the calculation processing can be easily performed.

In step S104Y, the calculation circuit 3Y outputs a signal showing the calculated concentration of the carbon dioxide to a control device (not shown). The signal showing the concentration of the carbon dioxide is used to control, for example, air conditioning in the control device.

Hereinabove, while the case using the approximate equation f has been described, when the table shown in FIG. 12 is used, the table is searched using the ratio (Ion/Ioff) calculated in step S102Y, and the corresponding concentration value may be output as an output value in step S104Y. In addition, when the graph shown in FIG. 13 is used, the concentration value corresponding to the ratio (Ion/Ioff) calculated in step S102Y is read out from the graph of FIG. 13, and the corresponding concentration value may be output as an output value in step S104Y.

(Operations and Effects of Fourth Embodiment)

Next, operations and effects of the gas concentration calculating device 1Y according to the fourth embodiment will be described. According to the gas concentration calculating device 1Y of the fourth embodiment, since the light receiving unit 50Y receives both of the direct light and the reflection light, inconvenience due to individual differences of the light receiving units 50Y when the direct light and the reflection light are received by the different light receiving units 50Y or when the lights in each case in which the reflectance is electrically modified by the modulation mirror 30Y are separately received by the different light receiving units 50Y, respectively, can be prevented.

In addition, in the fourth embodiment, a means for generating variation in optical path length and a difference in received light energy values of the light received by the light receiving unit 50Y is the modulation mirror 30Y, and an operation of the modulation mirror 30Y is performed under electrical control of the reflectance. Accordingly, since there is no vibration or the like to generate variation in optical path length or a difference in received light energy values and thus no position difference, additional noise, or the like due to the vibration, a decrease in optical detection accuracy of the gas concentration measuring module 2Y can be prevented.

In addition, as the modulation mirror 30Y electrically controls the reflectance, the reflectance switching can be rapidly performed. Accordingly, the time deviation in the optical measurement timing of the light received by the light receiving unit 50Y is negligible or remarkably short, and thus, pseudo-simultaneous measurement can be performed.

Accordingly, according to the fourth embodiment, inconvenience due to the individual difference of the light receiving unit 50Y, an error due to the vibration, and an error due to the time deviation can be prevented. In addition, an electro-optic device (EO device) or a liquid crystal optical element may be preferable as the modulation mirror 30Y having such effects.

In addition, the wavebands of the received lights can be modified to the same waveband by the band pass filter, and a decrease in optical detection accuracy can be prevented as the lights having different wavebands are received.

In addition, according to the fourth embodiment, based on the prepared database or approximate equation, the concentration of the target gas can be accurately calculated.

(Variant)

Hereinabove, while the fourth embodiment appropriate for the present invention has been described, it is needless to say that one aspect of the present invention is not limited to the fourth embodiment.

(First Variant)

For example, in the fourth embodiment, while the case in which the concentration of the carbon dioxide is calculated by the gas concentration calculating device 1Y has been described, it is needless to say that, as the wavelength of the light used for the measurement is varied, concentrations of the other gases can be calculated. In addition, according to kinds, measurement ranges, measurement accuracy, or the like of the gases, concentrations of which are to be measured, optimization with regard to a kind of the light source or a shape of the gas cell can be appropriately performed.

(Second Variant)

Figure 15:
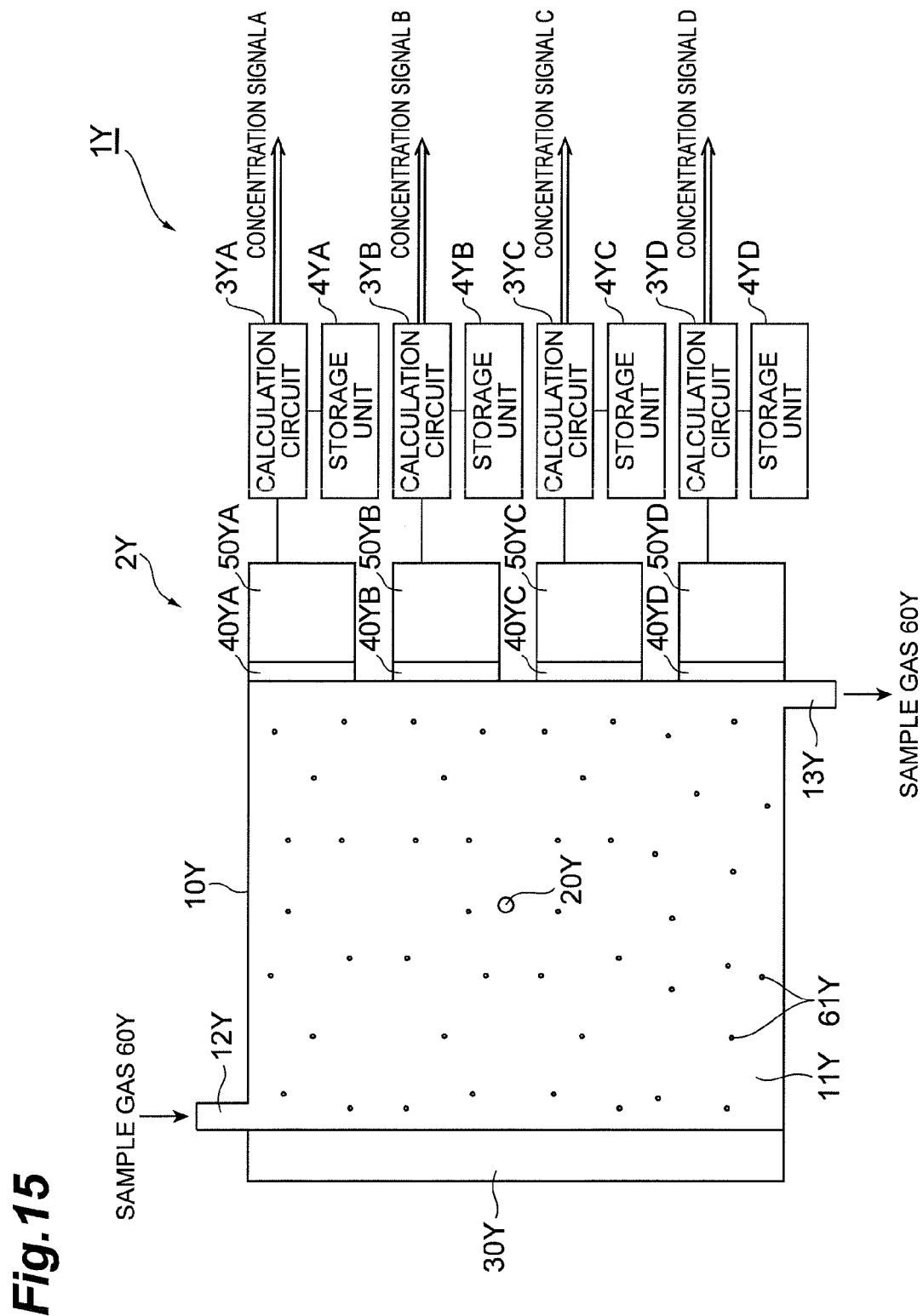
FIG. 15 is a schematic cross-sectional view showing a variant of the gas concentration calculating device 1Y.
Figure 16:
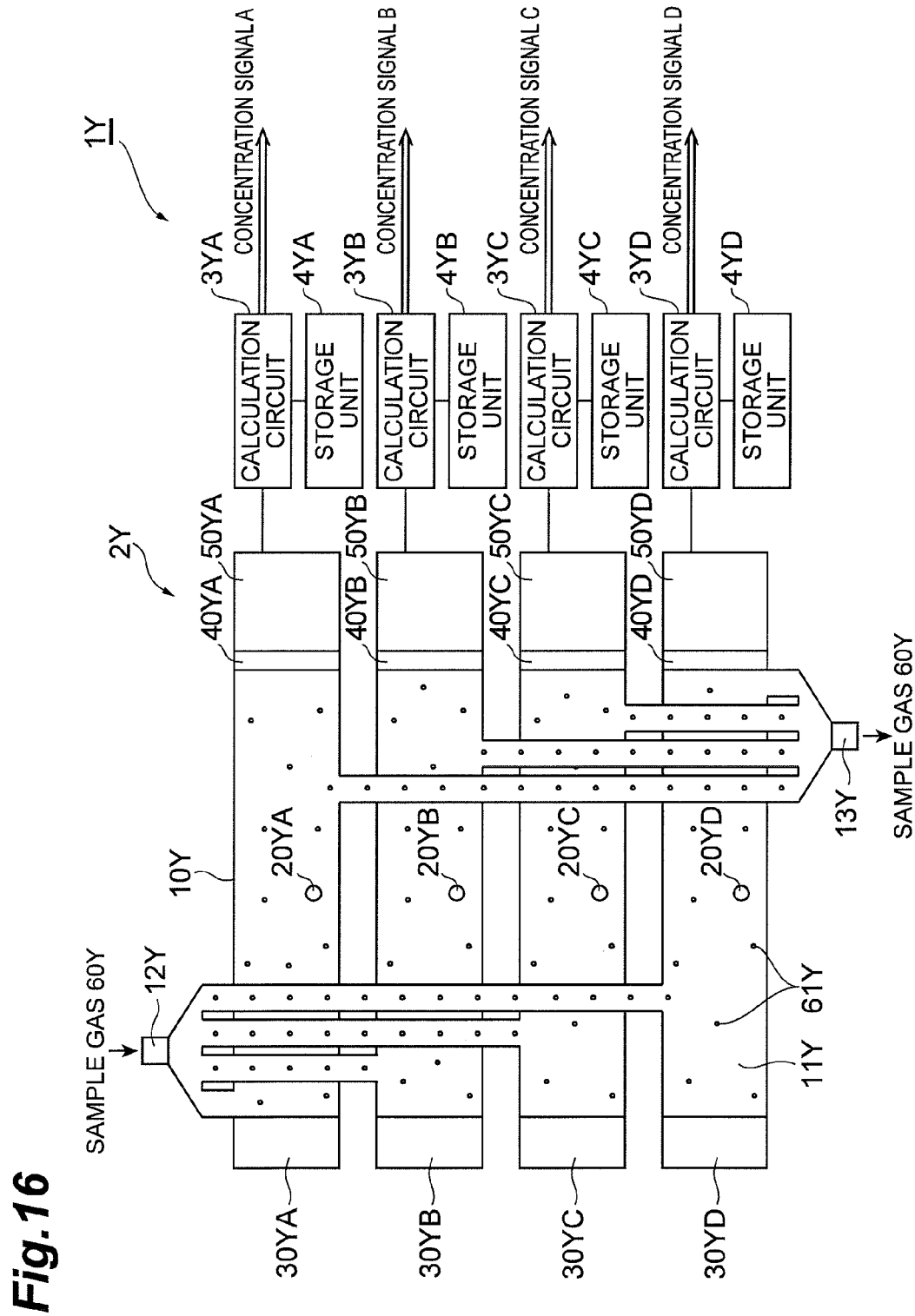
FIG. 16 is a schematic cross-sectional view showing a variant of the gas concentration calculating device 1Y.

FIGS. 15 and 16 show a variant for collectively processing and detecting gas concentrations of the sample gas 60Y in which a plurality of kinds of gases are mixed. In calculating the concentrations of the different kinds of gases as described above, while the respective gas concentrations should be measured using the wavelengths of the different gases, in the gas concentration measuring module of the application, a plurality of light receiving means are used and the gas concentration calculating module is installed at each light receiving means, and thus, measurement of the concentrations with respect to the plurality of kinds of gases can be collectively realized. That is, as shown in FIGS. 15 and 16, as a gas concentration measuring module 2Y including a plurality of light receiving means 50YA, 50YB, 50YC and 50YD corresponding to different target gases and a plurality of gas concentration calculating modules (calculation circuits 3YA, 3YB, 3YC and 3YD and storage units 4YA, 4YB, 4YC and 4YD) corresponding to the plurality of light receiving means 50YA, 50YB, 50YC and 50YD are provided, a plurality of gas concentrations in the sample gas 60Y in which a plurality of kinds of gases are mixed can be simultaneously detected.

FIGS. 15 and 16 illustrate an apparatus for measuring a gas concentration of each gas of the sample gas 60Y in which four kinds of gases are mixed. The light source configured to emit the light having a wavelength used for measurement is disposed in the gas cell 10Y. When a wavelength region of the emitted light is wide and includes a wavelength range that can be used to absorb each gas, as shown in FIG. 15, one light source 20Y can be used. As shown in FIG. 16, different kinds of light sources 20YA, 20YB, 20YC and 20YD configured to emit lights having wavelength regions detected by the respective light receiving means 50YA, 50YB, 50YC and 50YD may be installed at the light receiving means 50YA, 50YB, 50YC and 50YD, respectively. In addition, in the modulation mirror, when the wavelength region in which the reflectance can be controlled is small, as shown in FIG. 16, each ON-OFF control may be performed using four modulation mirrors 30YA, 30YB, 30YC and 30YD corresponding to the respective wavelengths used to absorb the respective gases.

In FIG. 15 and FIG. 16, in band pass filters 40YA, 40YB, 40YC and 40YD respectively disposed at the light receiving means 50YA, 50YB, 50YC and 50YD, the band pass filters 40YA, 40YB, 40YC and 40YD are different optical elements configured to allow transmission of the lights having wavelengths absorbed by the gases, which are to be measured by the light receiving means 50YA, 50YB, 50YC and 50YD, and are disposed at the light receiving means 50YA, 50YB, 50YC and 50YD, respectively. In addition, the sample gas 60Y is supplied to the gas cell 10Y, and measurement is performed. Further, in the calculation method of the gas concentration calculated for each of the light receiving means 50YA, 50YB, 50YC and 50YD, an algorithm thereof is the same as the above-mentioned algorithm. In addition, in FIG. 16, while the gas cell 10Y is configured to be divided into for each of the light receiving means 50YA, 50YB, 50YC and 50YD, the gas cell 10Y is not limited thereto but one common gas cell 10Y may be provided for all of the light receiving means 50YA, 50YB, 50YC and 50YD, as shown in FIG. 15.

(Third Variant)

In addition, the gas concentration calculating device 1Y may be configured such that the modulation mirror 30Y performs total reflection (Ron=1) and total transmission (Roff=0), and in this case, the following equation is satisfied.

$$Ion = I1(\rightarrow) + I2 = xI\exp(-KCL) + (((1-x)I\exp(-KCL)))\exp(-2KCL) \quad (15)$$

$$Ioff = I1(\rightarrow) = xI\exp(-KCL) \quad (16)$$

(Fourth Variant)

Further, in the fourth embodiment, in "when the reflectance is electrically modified by the reflectance modulation means" of the claims, while the case in which the modulation mirror 30Y is ON/OFF has been exemplarily described, it is not limited thereto, but, the case in which the reflectance is varied while the modulation mirror 30Y is kept ON may be applied as one example of "when the reflectance is electrically modified by the reflectance modulation means" of the claims.

(Fifth Variant)

Furthermore, the concentration of the gas calculated by the gas concentration calculating device 1Y can be applied to various instruments configured to calculate the concentration of the gas, in addition to control of air conditioning.

[Fifth Embodiment]

(Overall Configuration of Gas Concentration Calculating Device 1Z)

Figure 17:
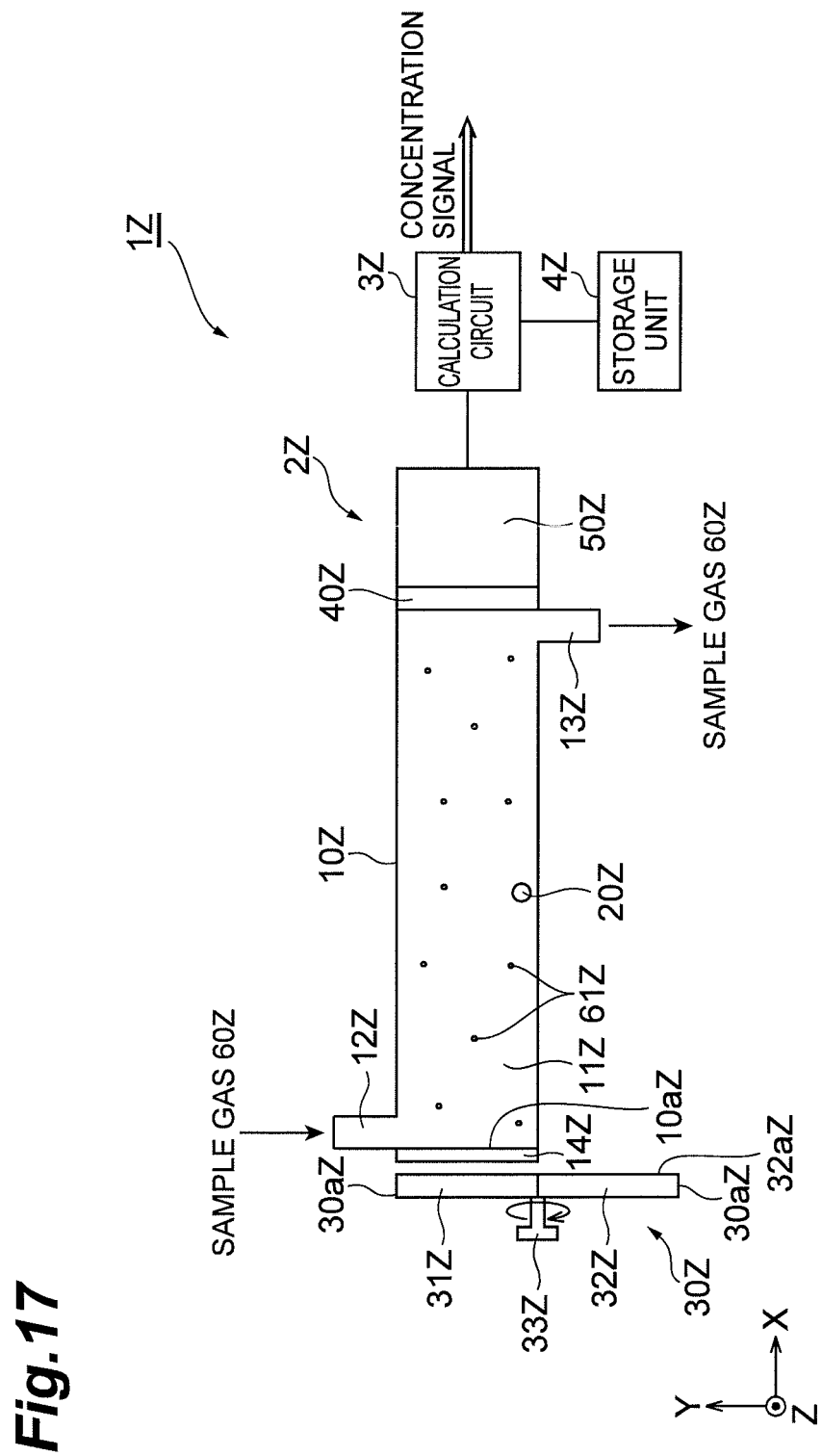
FIG. 17 is a schematic cross-sectional view showing a gas concentration calculating device 1Z according to a fifth embodiment of the present invention.

First, an overall configuration of the gas concentration calculating device 1Z according to a fifth embodiment will be described. FIG. 17 is a schematic cross-sectional view showing the gas concentration calculating device 1Z. The gas concentration calculating device 1Z includes a gas concentration measuring module 2Z configured to receive light from a light source 20Z to measure an energy value thereof, a calculation circuit 3Z (corresponding to "a gas concentration calculating module" of the claims) configured to calculate a gas concentration based on a measurement result by the gas concentration measuring module 2Z, and a storage unit 4Z (corresponding to "a storage means" of the claims) configured to store information needed when the calculation circuit 3Z calculates the gas concentration, calculating a concentration of a target gas. The gas concentration calculated by the calculation circuit 3Z is output to a control device (not shown) to be used to control, for example, an air-conditioning system, and so on. In addition, in the fifth embodiment, the case in which carbon dioxide in a sample gas 60Z introduced into the gas concentration measuring module 2Z is provided as a target gas for concentration calculation will be described.

The gas concentration measuring module 2Z includes a gas cell 10Z, the light source 20Z, a rotating mirror 30Z (corresponding to "a rotary mechanism" of the claims), a band pass filter 40Z, and a light receiving unit 50Z (corresponding to "a light receiving means" of the claims).

The gas cell 10Z is configured to form an introduction space 11Z into which the sample gas 60Z is introduced. The gas cell 10Z has a gas introduction unit 12Z installed at one end side of the gas cell 10Z configured to introduce the sample gas 60Z into the introduction space 11Z, and a gas discharge unit 13Z installed at the other end side of the gas cell 10Z and configured to discharge the sample gas 60Z in the introduction space 11Z to the outside. The gas discharge unit 13Z may have a plurality of holes formed in an inner wall (for example, a bottom portion) of the gas cell.

The light source 20Z is disposed in the gas cell 10Z and configured to emit infrared rays. In the fifth embodiment, a light source configured to emit light including light having a wavelength range of 4.2 μm to 4.3 μm is used as the light source 20Z. In FIG. 17, while an example in which the light source 20Z is disposed at a bottom portion of a center in the gas cell 10Z has been shown, it is not limited thereto but the light source 20Z may be disposed at a top portion or a center portion of the center in the gas cell 10Z or may be disposed at the rotating mirror 30Z side or the light receiving unit 50Z side in an offset manner. The infrared rays from the light source 20Z are absorbed and attenuated by carbon dioxide molecules 61Z in the sample gas 60Z.

The rotating mirror 30Z is disposed at one end 10aZ side of the gas cell 10Z and rotated to allow reflection or transmission of the light emitted from the light source 20Z. The rotating mirror 30Z is rotated or moved in a direction different from a direction of an optical path from the light source 20Z to the light receiving unit 50Z to allow reflection or transmission of the light. In an XYZ coordinate system shown in FIG. 17, the direction of the optical path from the light source 20Z to the light receiving unit 50Z is an X direction, and rotation of the rotating mirror 30Z is performed along a YZ surface. That is, the rotating mirror 30Z is rotated on a YZ surface perpendicular to the X direction, which is the direction of the optical path. In FIG. 17, rotation of the rotating mirror 30Z on the YZ surface is designated by an arrow. In other words, in this case, while the direction of the optical path and the rotation axis of the rotating mirror 30Z are equal to the X direction, an end portion 30aZ of the rotating mirror 30Z is rotated to draw a circle on the YZ surface. In addition, according to an apparatus configuration, the direction of the optical path and the rotation axis of the rotating mirror 30Z may be substantially the same direction. The rotating mirror 30Z is not moved along the X direction, which is the direction of the optical path. In the fifth embodiment, the rotating mirror 30Z is constituted by a reflecting plate 31Z and a hole 32Z, and controls a rotational direction, a rotational speed, or the like, using a rotary drive mechanism 33Z. The hole 32Z is a space surrounded by a frame 32aZ. A window 14Z formed of a material having a high permeability with respect to the infrared ray is installed at the one end 10aZ side of the gas cell 10Z.

The band pass filter 40Z is disposed on the optical path between the light source 20Z and the light receiving unit 50Z, and allows transmission of the light having a predetermined wavelength only. In the fifth embodiment, the band pass filter 40Z is disposed at an end of the light receiving unit 50Z side of the gas cell 10Z and configured to allow transmission of the light having a wavelength range of 4.2 µm to 4.3 µm only.

The light receiving unit 50Z is a light receiving element disposed at the other end of the gas cell 10Z and configured to receive both of a direct light directly emitted from the light source 20Z and a reflection light emitted from the light source 20Z and reflected by the rotating mirror 30Z. That is, one light receiving unit 50Z receives both of the direct light and the reflection light. In other words, one light receiving unit 50Z receives the light in each case in which the light is reflected by or passes through the rotating mirror 30Z (as described below, the direct light, and a sum of the direct light and the reflection light). Accordingly, in comparison with the case in which the plurality of light receiving means are used to receive the plurality of kinds of lights, respectively, there is no bad effect due to individual differences of the light receiving means.

(Structure for Generating Difference in Optical Path Length or Received Light Energy Value)

In the fifth embodiment, FIG. 18 is a view for describing a structure for generating a difference in optical path length or the received light energy value. Similar to FIG. 17, variation in optical path length and the received energy of the light emitted from the light source 20Z disposed at the bottom portion of the center of the gas cell 10Z and arriving at the light receiving unit 50Z is performed by rotation of the rotating mirror 30Z. In the description, for the convenience of description, modification of the reflectance through the total reflection or the total transmission of the rotating mirror 30Z is described.

FIG. 18(A) shows a situation in which the reflecting plate 31Z is disposed to face the light source 20Z at the one end 10aZ side of the gas cell 10Z by rotation of the rotating mirror 30Z and the light arriving from the light source 20Z is totally reflected in the gas cell 10Z. In FIG. 18(A), the direct light, which is a light emitted from the light source 20Z and directly arriving at the light receiving unit 50Z, is designated by I1 (→), and a length of the optical path through which the direct light passes is about L. In addition, the reflection light is designated by I1 (←) (the light emitted from the light source 20Z and arriving at the reflecting plate 31Z) and I2 (the light reflected by the reflecting plate 31Z and arriving at the light receiving unit 50Z), and a length of the optical path through which the reflection light passes is 3L (L+2L). In a state in which the reflecting plate 31Z is disposed to face the light source 20Z, both of the direct light and the reflection light arrive at the light receiving unit 50Z via the optical paths of L and 3L, respectively, and the received light energy values are measured. Meanwhile, FIG. 18(B) shows a situation in which the hole 32Z is positioned to face the light source 20Z at the one end 10aZ side of the gas cell 10Z by rotation of the rotating mirror 30Z, and the light arriving from the light source 20Z is transmitted, without being reflected at all. In this case, only the direct light arrives at the light receiving unit 50Z via the optical path of about L, and the received light energy value is measured. In addition, while FIG. 18(B) shows that the non-reflected light is transmitted through the hole 32Z, it is not limited thereto but the light may be absorbed. In this case, instead of the hole 32Z, an absorbing body (not shown) may be provided.

As described above, in the fifth embodiment, variation in optical path length and the received light energy value is performed by rotation of the rotating mirror 30Z in a direction different from a lengthwise direction of the optical path. For this reason, in order to generate the variation in optical path length or a difference in received light energy values, there is no necessity to perform movement of the rotating mirror 30Z in the lengthwise direction of the optical path. That is, while the rotating mirror 30Z is being rotated with no movement in the lengthwise direction of the optical path, there is no variation in absolute distance between the rotating mirror 30Z and the light receiving unit 50Z. Accordingly, since the optical path length is stable, even when the rotating mirror 30Z is not temporarily stopped, measurement with high accuracy can be realized. As a result, a large time deviation in optical measurement timing due to temporary movement stoppage of the rotating mirror 30Z can be prevented.

(Stored Information of Storage Unit 4Z)

Next, information stored in the storage unit 4Z will be described. A database or an approximate equation showing a correlation between a ratio of the received light energy values of the light receiving unit 50Z and the concentration of the carbon dioxide, which is the target gas, in each case in which the light is reflected by or passes through the rotating mirror 30Z, is previously stored in the storage unit 4Z.

Figure 19:
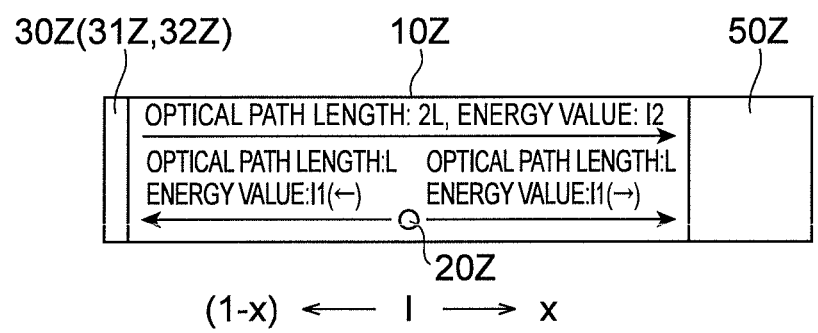
FIG. 19 is a view for describing stored information of a storage unit 4Z.

FIG. 19 is a view for describing the stored information of the storage unit 4Z. While FIG. 19 is basically similar to FIG. 17 or 18, only necessary elements for the following description are included, and the optical path length is schematically designated by L or 2L. In FIG. 19, the following Equations (1) to (3) are satisfied.

$$I = I1(\rightarrow) + I1(\leftarrow) \tag{1}$$

$$I1(\rightarrow)/I = x \tag{2}$$

$$I1(\leftarrow)/I = 1-x \tag{3}$$

Here, I is a total energy value of infrared rays emitted from the light source 20Z, I1 (→) is an energy value of the infrared rays, which are the direct light, emitted from the light source 20Z in a rightward direction in FIG. 19, I1 (←) is an energy value of the infrared rays emitted from the light source 20Z in a leftward direction in FIG. 19, and x is a distribution ratio of I1 (→) and I1 (←).

In FIG. 19, when the reflecting plate 31Z is disposed to face the light source 20Z at the one end 10aZ side of the gas cell 10Z by rotation of the rotating mirror 30Z (in a state of FIG. 18(A)), according to Lambert-Beer's Law, the following Equations (4) to (7) are satisfied.

$$I1(\rightarrow) = xI\exp(-KCL) \tag{4}$$

$$I1(\leftarrow) = (1-x)I\exp(-KCL) \tag{5}$$

$$I2 = (I1(\leftarrow)Ron)\exp(-2KCL) = (((1-x)I\exp(-KCL))Ron) \exp(-2KCL) \tag{6}$$

$$Ion = I1(\rightarrow) + I2 = xI\exp(-KCL) + (((1-x)I\exp(-KCL))Ron) \exp(-2KCL) \tag{7}$$

Here, K is an absorption coefficient, C is a concentration of carbon dioxide in the sample gas 60Z introduced into the gas cell 10Z, L is a distance from the light source 20Z to the light receiving unit 50Z, 2L is a distance from the rotating mirror 30Z (the reflecting plate 31Z) to the light receiving unit 50Z, I2 is an energy value of the infrared rays, which are a reflection light, emitted from the light source 20Z in a leftward direction and reflected by the rotating mirror 30Z (the reflecting plate 31Z), Ron is a reflectance of the rotating mirror 30Z

(the reflecting plate 31Z) in this state, and Ion is a total energy of the infrared rays arriving at the light receiving unit 50Z in this state, i.e., a sum energy value of the direct light and the reflection light.

In addition, in FIG. 19, when the hole 32Z is disposed to face the light source 20Z at the one end 10aZ side of the gas cell 10Z by rotation of the rotating mirror 30Z (in a state of FIG. 18(B)), according to Lambert-Beer's Law, the following Equations (8) to (11) are satisfied.

$$I1(\rightarrow)=xI\exp(-KCL) \quad (8)$$

$$I1(\leftarrow)=(1-x)I\exp(-KCL) \quad (9)$$

$$I2=(I1(\leftarrow)Roff)\exp(-2KCL)=(((1-x)I\exp(-KCL))Roff)\exp(-2KCL) \quad (10)$$

$$Ioff=I1(\rightarrow)+I2=xI\exp(-KCL)+(((1-x)I\exp(-KCL))Roff)\exp(-2KCL) \quad (11)$$

Here, Roff is a reflectance of the rotating mirror 30Z (the hole 32Z), and Roff is basically 0 since the rotating mirror 30Z is the hole 32Z. Ioff is a total energy of the infrared ray arriving at the light receiving unit 50Z in this state, i.e., an energy value of the direct light only due to presence of the hole 32Z, with no reflection light.

A ratio between the energy value Ion of the light received by the light receiving unit 50Z in a state in which the reflecting plate 31Z faces the light source 20Z and the energy value Ioff of the light received by the light receiving unit 50Z in a state in which the hole 32Z faces the light source 20Z (corresponding to "a ratio of the received light energy values of the light receiving means in each case in which the light is reflected or transmitted by a rotary mechanism" of the claims) is as follows.

$$Ion/Ioff=[xI\exp(-KCL)+(((1-x)I\exp(-KCL))Ron)\exp(-2KCL)]/[xI\exp(-KCL)+(((1-x)I\exp(-KCL))Roff)\exp(-2KCL)] \quad (12)$$

Here, Roff=0 and x=0.5, i.e., the hole 32Z faces the light source 20Z to allow total transparency (total transmission), and when distribution of the light source 20Z becomes half, a ratio between Ion and Ioff satisfies the following Equation.

$$Ion/Ioff=(1+(Ron)\exp(-2KCL)) \quad (13)$$

Here, since Ron, K and L are constant according to equipment configuration, Equation (13) can be rewritten as follows.

$$C=f(\text{Ratio(transparent mirror)}) \quad (14)$$

Here, Ratio (transparent mirror) is a ratio of Ion and Ioff when Roff=0 and x=0.5, and f is a function, which is an approximate equation showing a correlation between Ratio (transparent mirror) and the concentration C. The storage unit 4Z stores information showing an approximate equation f of Equation (14).

Meanwhile, instead of obtaining the approximate equation f, using already known I, K, C, L, x, Ron and Roff and using Equation (7) or (11), Ion or Ioff in each case may be calculated, and a ratio Ion/Ioff may be calculated. Then, the result is used to draft a database as a table. FIG. 20 shows one example of the database drafted as described above. In the database of FIG. 20, concentrations of carbon dioxide corresponding to the respective values of Ion/I, Ioff/I and Ion/Ioff are shown.

Figure 21:
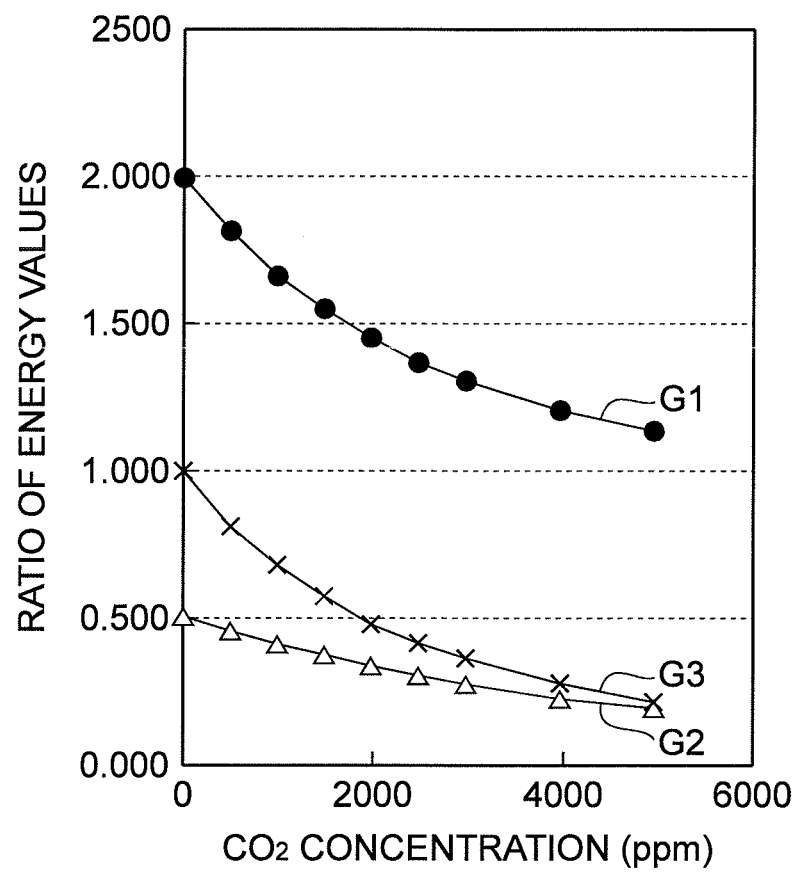
FIG. 21 is a view showing one example of a graph stored in the storage unit 4Z.

In addition, using the database of FIG. 20, a graph shown in FIG. 21 may be obtained. The graphs shown in FIG. 21 show correlations between the concentrations of carbon dioxide and the ratios Ion/Ioff. In FIG. 21, G1 is a graph showing a correlation between the concentration of carbon dioxide and the ratio Ion/Ioff, G2 is a graph showing a correlation between the concentration of carbon dioxide and the ratio Ion/I, and G3 is a graph showing a correlation between the concentration of carbon dioxide and the ratio Ioff/I. The storage unit 4Z stores information showing the above-mentioned database or graph. In addition, in FIG. 20 or 21, in order to easily understand the database or the graph, when the concentration of the carbon dioxide is zero ppm, while the graph shows that Ion/Ioff becomes 2, the ratio of each energy value with respect to the energy value I emitted from the light source, Ion/I becomes 1, Ioff/I becomes 0.5, and I1($\rightarrow$)/I, I1($\leftarrow$)/I and I2/I become 0.5, in actual measurement, since the energy I emitted from the light source cannot be measured, among the values shown in the database or the graph, the value obtained as a measurement value is only the ratio Ion/Ioff of the energy values.

As described above, based on the approximate equation f of Equation (14), the database of FIG. 20 or the graph of FIG. 21, since the correlation between the concentration of the carbon dioxide and Ion/Ioff can be known, when Ion/Ioff is measured, the concentration of the carbon dioxide can be calculated.

(Concentration Calculation Processing of Carbon Dioxide)

Figure 22:
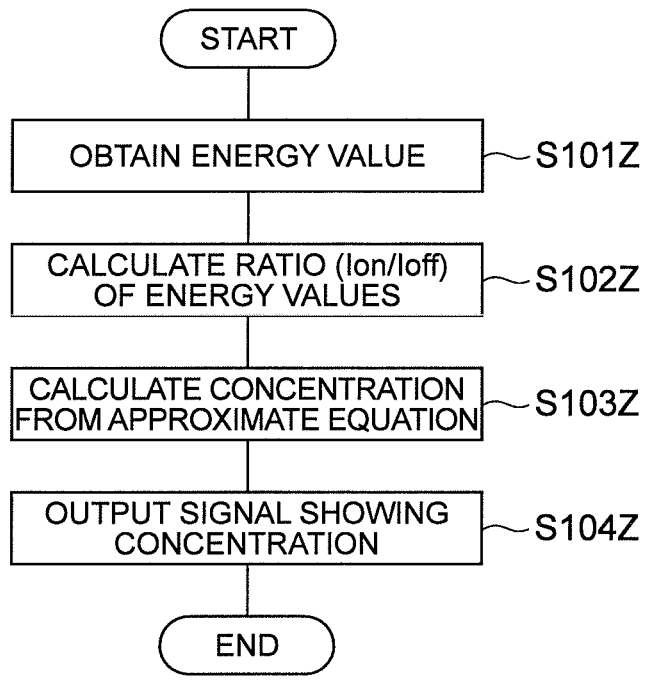
FIG. 22 is a flowchart showing a flow of carbon dioxide concentration calculation processing by the gas concentration calculating device 1Z.

Next, a flow of processing of calculating a concentration of carbon dioxide using the calculation circuit 3Z from the energy value of the light received by the light receiving unit 50Z will be described. The calculation circuit 3Z is a computation circuit configured to calculate the concentration of the carbon dioxide corresponding to the ratio based on the ratio (the Ion/Ioff) of the received light energy values of the light receiving unit 50Z and based on the above-mentioned approximate equation f, the database of FIG. 20 or the graph of FIG. 21, in each case in which the light is reflected or transmitted by the modulation mirror 30Z, and including a CPU, and so on. FIG. 22 is a flowchart showing a flow of the carbon dioxide concentration calculation processing.

In step S101Z, the calculation circuit 3Z obtains the energy value Ion of the light received by the light receiving unit 50Z in a state in which the reflecting plate 31Z faces the light source 20Z and the energy value Ioff of the light received by the light receiving unit 50Z in a state in which the hole 32Z faces the light source 20Z.

Next, in step S102Z, the calculation circuit 3Z calculates a ratio (Ion/Ioff) between the energy value Ion and the energy value Ioff. In step S103Z, the calculation circuit 3Z calculates the concentration of the carbon dioxide from the ratio (Ion/Ioff) calculated in step S103Z using the approximate equation f stored in the storage unit 4Z. As the concentration is calculated using the approximate equation f, calculation processing can be easily performed.

In step S104Z, the calculation circuit 3Z outputs a signal showing the calculated concentration of the carbon dioxide to a control device (not shown). The signal showing the concentration of the carbon dioxide is used to control, for example, air conditioning in a control device.

As described above, while the case in which the approximate equation f is used has been described, when the table shown in FIG. 20 is used, the table is searched using the ratio (Ion/Ioff) calculated in step S102Z, and a corresponding concentration value may be output as an output value in step S104Z. In addition, when the graph of FIG. 21 is used, the concentration corresponding to the ratio (Ion/Ioff) calculated in step S102Z may be read out from the graph of FIG. 21, and the concentration value may be output as an output value in step S104Z.

(Operations and Effects of Fifth Embodiment)

Next, operations and effects of the gas concentration calculating device 1Z according to the fifth embodiment will be described. According to the gas concentration calculating device 1Z of the fifth embodiment, since the light receiving unit 50Z receives both of the direct light and the reflection light, inconvenience due to individual differences of the light receiving units 50Z when the direct light and the reflection light are received by the different light receiving units 50Z, respectively, or when the lights reflected or transmitted by the rotating mirror 30Z are separately received by the different light receiving units 50Z, respectively, can be prevented.

In addition, in the fifth embodiment, a means for generating variation in optical path length or a difference in received light energy values of the lights received by the light receiving unit 50Z is the rotating mirror 30Z, and the rotating mirror 30Z is rotated in a direction different from a direction of the optical path from the light source 20Z to the light receiving unit 50Z to allow reflection or transmission of the light. Here, "the rotation in the direction different from the direction of the optical path" becomes possible, for example, as a rotation axis of the rotating mirror 30Z is in the same direction as the optical path. That is, in order to generate the variation in optical path length or the difference in received light energy values, there is no need to perform movement of the rotating mirror 30Z in the direction of the optical path, and for this reason, even when the rotating mirror 30Z is rotated, there is no variation in absolute distance between the rotating mirror 30Z and the light receiving unit 50Z. Accordingly, for example, unlike the case in Patent Document 2, since the optical path length is stable, there is no need to temporarily stop the rotating mirror 30Z. As a result, generation of the large time deviation in the measurement timing of the light due to temporary movement stoppage of the rotating mirror 30Z can be prevented.

As described above, according to the fifth embodiment, inconvenience due to the individual differences of the light receiving units 50Z or inconvenience due to movement of the element for varying the optical path length in the same direction as the direction of the optical path can be prevented.

In addition, according to the fifth embodiment, the rotating mirror 30Z constituted by the reflecting plate 31Z and the hole 32Z can be provided as a simple configuration, the rotating mirror 30Z can be rotated in a direction substantially perpendicular to the direction of the optical path, and thus, reflection and transmission of the light can be clearly switched.

Further, the waveband of the received light can become the same waveband by the band pass filter, and a decrease in optical detection accuracy can be prevented as the lights having different wavebands are received.

Furthermore, according to the fifth embodiment, based on the prepared database or approximate equation, the concentration of the target gas can be accurately calculated.

[Sixth Embodiment]

Next, a sixth embodiment of the present invention will be described. A gas concentration calculating device 1ZA of the sixth embodiment is distinguished from the fifth embodiment in that a means for generating variation in optical path length or a difference in received light energy values of the lights received by the light receiving unit 50Z is replaced with a MEMS actuator 70Z, instead of the rotating mirror 30Z. Hereinafter, differences will be mainly described.

(Overall Configuration of Gas Concentration Calculating Device 1ZA)

FIG. 23(A) is a schematic cross-sectional view showing the gas concentration calculating device 1ZA. The MEMS actuator 70Z is disposed at one end 10aZ side of a gas cell 10Z, and allows reflection or transmission of light emitted from a light source 20Z by rotating a mirror 71Z to a certain angle. Here, "reflection" means that the light from the light source 20Z is reflected in the gas cell 10Z, and "transmission" means that the light from the light source 20Z passes out of the gas cell 10Z, not being reflected in the gas cell 10Z, or is reflected out of the gas cell 10Z. Hereinafter, for the convenience of description, "transmission" is described to mean that the light is reflected out of the gas cell 10Z. In addition, rotation of the MEMS actuator 70Z means that the mirror 71Z is rotated by the MEMS actuator 70Z.

Figure 23:
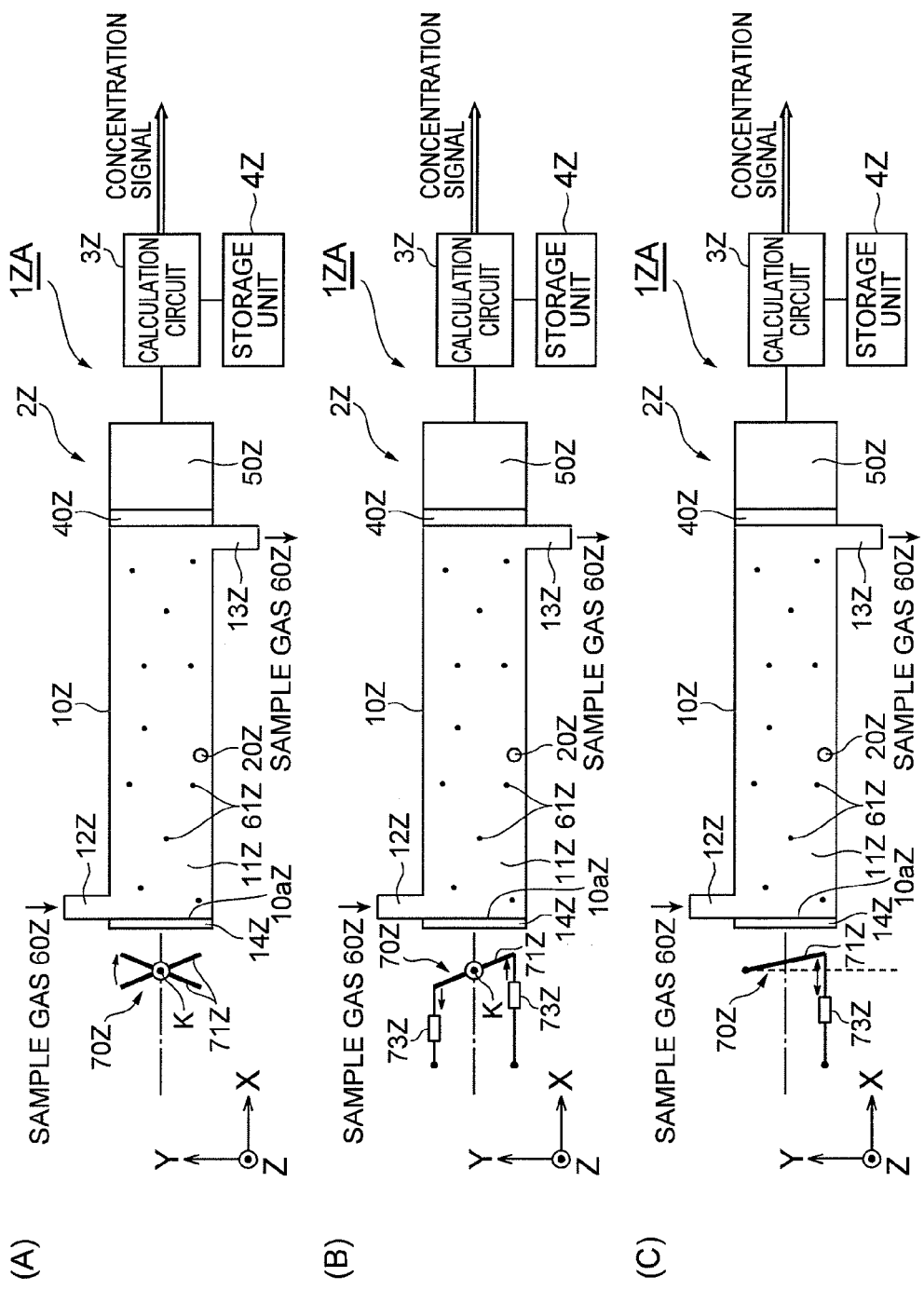
FIG. 23 is a schematic cross-sectional view showing a gas concentration calculating device 1ZA according to a sixth embodiment of the present invention.

The MEMS actuator 70Z allows reflection or transmission of the light as the mirror 71Z is rotated or moved in a direction different from a direction of an optical path from the light source 20Z to the light receiving unit 50Z. In an XYZ coordinate system shown in FIG. 17, the direction of the optical path from the light source 20Z to the light receiving unit 50Z is an X direction, and the mirror 71Z of the MEMS actuator 70Z is rotated to a certain angle about an axis K as a rotation axis, which is different from an X-axis by a predetermined angle $\phi$. In FIG. 23, rotation of the mirror 71Z is designated by an arrow. The MEMS actuator 70Z is not moved in the X direction, which is the direction of the optical path. A rotational direction, a rotational speed, or the like of the MEMS actuator 70Z is controlled by a rotary drive mechanism (not shown). A window 14Z formed of a material having a high permeability with respect to the infrared rays is installed at the one end 10aZ of the gas cell 10Z. In reality, as shown in FIG. 23(B), the MEMS actuator 70Z includes actuator elements 73Z installed at both ends of the mirror 71Z to move in the X direction, one moving in a +X direction and the other moving in a −X direction, and the mirror 71Z is rotated to a certain angle only, with no movement in a position of a center of the mirror 71Z in the X direction. As the light from the light source 20Z is reflected by a center of the mirror 71Z, even when rotation of the mirror 71Z, i.e., rotation of the MEMS actuator 70Z, is performed, variation in distance in the X direction between the light source 20Z and the mirror 71Z and between the mirror 71Z and the light receiving unit 50Z is constantly maintained, with no variation. In addition, since the MEMS actuator 70Z is smaller in size than the rotating mirror 30Z of the fifth embodiment, as shown in FIG. 23(C), even when the actuator element 73Z is installed at one end, rather than both ends of the mirror 71Z, and the other end is fixed, in reality, variation in distance in the X direction between the light source 20Z and the mirror 71Z and between the mirror 71Z and the light receiving unit 50Z may be constant with no variation.

(Structure for Generating Difference in Optical Path Length or Received Light Energy Value)

FIG. 24 is a view for describing a structure for generating a difference in optical path length or received light energy value in the sixth embodiment. Variation in optical path length and the received light energy value of the light emitted from the light source 20Z and arriving at the light receiving unit 50Z is performed by rotation of the MEMS actuator 70Z. In the description, for the convenience of description, as the entire light input by the MEMS actuator 70Z is reflected into or out of the gas cell 10Z, modification of the reflectance will be described.

FIG. 24(A) shows a situation in which all of the light arriving from the light source 20Z is reflected into the gas cell 10Z by rotation of the mirror 71Z of the MEMS actuator 70Z. In FIG. 24(A), a direct light, which is a light emitted from the light source 20Z that directly arrives at the light receiving unit 50Z, is designated by l1 (→), and a length of the optical path through which the direct light passes is about L. In addition, a reflection light is designated by I1 (←) (the light emitted from the light source 20Z and arriving at the mirror 71Z of the MEMS actuator 70Z) and I2 (the light reflected by the mirror 71Z of the MEMS actuator 70Z and arriving at the light receiving unit 50Z), and a length of the optical path through which the reflection light passes is about 3L (L+2L). In a state in which the mirror 71Z of the MEMS actuator 70Z reflects all of the light from the light source 20Z into the gas cell 10Z, both of the direct light and the reflection light arrive at the light receiving unit 50Z via the optical paths of L and 3L, respectively, and the received light energy values are measured. Meanwhile, FIG. 24(B) shows a situation in which all of the light arriving from the light source 20Z is reflected out of the gas cell 10Z by rotation of the mirror 71Z of the MEMS actuator 70Z. In this case, only the direct light arrives at the light receiving unit 50Z via the optical path of L, and the received light energy value is measured.

As described above, in the sixth embodiment, variation in optical path length and the received light energy value is performed by rotation of the mirror 71Z of the MEMS actuator 70Z in a direction different from the lengthwise direction of the optical path. For this reason, in order to generate the variation in optical path length or the difference in received light energy values, there is no need to perform movement of the mirror 71Z in the lengthwise direction of the optical path. That is, since the mirror 71Z is rotated with no movement in the lengthwise direction of the optical path, there is no variation in absolute distance between the mirror 71Z and the light receiving unit 50Z. Accordingly, since the optical path length is stable, even when the mirror 71Z is not temporarily stopped, measurement with high accuracy can be realized. As a result, generation of the large time deviation in the measurement timing of the light due to temporary movement stoppage of the mirror 71Z can be prevented.

In addition, according to the sixth embodiment, as the MEMS actuator 70Z is used, rapid rotation becomes possible while suppressing vibrations upon rotation. Accordingly, a decrease in optical detection accuracy due to the vibrations can be prevented. Further, as the mirror 71Z of the MEMS actuator 70Z is rapidly rotated, switching of reflection and transmission (reflection out of the gas cell 10Z) of the light can be rapidly performed, the time deviation in the optical measurement timing of the light received by the light receiving unit 50Z is negligible or remarkably short, and thus, pseudo-simultaneous measurement can be performed.

(Variant)

As described above, while an exemplary embodiment according to still another aspect of the present invention has been described, it is needless to say that still another aspect of the present invention is not limited to the fifth and sixth embodiments. For example, in the fifth and sixth embodiments, while the case in which the concentration of the carbon dioxide is calculated by the gas concentration calculating device 1Z or 1ZA has been described, it is needless to say that, by varying the wavelength of the light used for measurement, concentrations of other gases can be calculated. In addition, according to kinds, measurement ranges, measurement accuracy, or the like of the gases, concentrations of which are to be measured, optimization with regard to a kind of the light source or a shape of the gas cell can be appropriately performed.

FIG. 25 shows a variant for detecting gas concentrations of the sample gas 60Z, in which a plurality of kinds of gases are mixed, through collective processing. In calculating the concentrations of the different kinds of gases as described above, while there is a need to measure various gas concentrations using wavelengths of different lights, in the gas concentration measuring module of the application, as a plurality of light receiving means are used and the gas concentration calculating module is installed at each light receiving means, measurement of concentrations of a plurality of kinds of gases can be realized through collective processing. That is, as shown in FIG. 25, the gas concentration measuring module 2Z including a plurality of light receiving means 50ZA, 50ZB, 50ZC and 50ZD corresponding to different target gases and a plurality of gas concentration calculating modules (calculation circuits 3ZA, 3ZB, 3ZC and 3ZD and storage units 4ZA, 4ZB, 4ZC and 4ZD) corresponding to the plurality of light receiving means 50ZA, 50ZB, 50ZC and 50ZD are provided, and thus a plurality of gas concentrations in the sample gas 60Z, in which a plurality of kinds of gases are mixed, can be simultaneously detected.

FIG. 25 illustrates an example of an apparatus for measuring a gas concentration of each gas in the sample gas 60Z, in which four kinds of gases are mixed. A light source configured to emit light having a wavelength used for measurement is disposed in the gas cell 10Z. When the wavelength region of the emitted light is wide and includes a wavelength range that can be used for absorption of each gas, as shown in FIG. 23, one light source 20Z can be used. In addition, while not shown, different kinds of light sources 20ZA, 20ZB, 20ZC and 20ZD configured to emit lights having wavelength regions detected by the light receiving means 50ZA, 50ZB, 50ZC and 50ZD may be installed at the light receiving means 50ZA, 50ZB, 50ZC and 50ZD, respectively.

In FIG. 25, band pass filters 40ZA, 40ZB, 40ZC and 40ZD respectively disposed at the light receiving means 50ZA, 50ZB, 50ZC and 50ZD are optical elements configured to transmit the light having a wavelength absorbed by gases to be measured at the light receiving means 50ZA, 50ZB, 50ZC and 50ZD and block the light having other wavelengths, and the different band pass filters 40ZA, 40ZB, 40ZC and 40ZD are disposed at the light receiving means 50ZA, 50ZB, 50ZC and 50ZD, respectively. In addition, the sample gas 60Z is supplied into the gas cell 10Z, and measurement is performed. Further, the calculation method of the gas concentrations calculated by each of the light receiving means 50ZA, 50ZB, 50ZC and 50ZD uses the same algorithm as described above. Furthermore, in FIG. 25, while the sixth embodiment is applied for a multi-system, the fifth embodiment may be applied for a multi-system. Here, a rotary mechanism may be shared between upper and lower gas concentration measuring modules, one side may reflect light and the other side may transmit the light.

In addition, in the fifth and sixth embodiments, while the case in which the rotating mirror 30Z or the MEMS actuator 70Z performs total reflection or total transmission has been described as one example, it is not limited thereto but an apparatus for allowing reflection or transmission with a certain level of reflectance or transmittance may be provided.

In addition, the concentration of the gas calculated by the gas concentration calculating device 1Z or 1ZA can be applied to various instruments for calculating a concentration of a gas, in addition to control of air conditioning.

Reference Signs List 1X, 1XA to 1XE . . . gas concentration calculating device, 2X, 2XA, 2XB . . . gas concentration measuring module, 3X, 3XA to 3XD . . . calculation circuit, 10X . . . gas cell, 11X . . . introduction space, 20X . . . infrared light source, 20XA to 20XD . . . light source, 30X . . . light receiving unit, 40X . . . saturated gas chamber, 41X . . . saturated gas, 50X . . . sample gas, 60X, 60XA . . . reflecting mirror, 70X . . . modulation mirror, 80X . . . rotating mirror, 81X . . .

reflecting plate, 82X ... hole, 90X ... band pass filter, 100X, 100XA, 100XB, 200XA to 200XD, 300XA to 300XD ... reflection switching unit

1Y ... gas concentration calculating device, 2Y ... gas concentration measuring module, 3Y ... calculation circuit, 4Y ... storage unit, 10Y ... gas cell, 11Y ... introduction space, 12Y ... gas introduction unit, 13Y ... gas discharge unit, 20Y ... light source, 30Y ... modulation mirror, 40Y ... band pass filter, 50Y ... light receiving unit, 60Y ... sample gas

1Z ... gas concentration calculating device, 2Z ... gas concentration measuring module, 3Z ... calculation circuit, 4Z ... storage unit, 10Z ... gas cell, 11Z ... introduction space, 12Z ... gas introduction unit, 13Z ... gas discharge unit, 20Z ... light source, 30Z ... reflecting mirror, 40Z ... band pass filter, 50Z ... light receiving unit, 60Z ... sample gas, 70Z ... MEMS actuator, 71Z ... mirror Industrial Applicability It is an aspect of the present invention to provide a gas concentration calculating device and a gas concentration measuring module that are capable of preventing inconvenience due to individual differences of the light receiving elements and preventing inconvenience due to instability of the optical path length.

It is another aspect of the present invention to provide a gas concentration calculating device and a gas concentration measuring module that are capable of preventing inconvenience due to individual differences of the light receiving elements, preventing a decrease in optical detection accuracy due to vibrations of the element for varying the optical path length, and suppressing a decrease in optical detection accuracy due to the measurement time deviation of the light.

It is still another aspect of the present invention to provide a gas concentration calculating device and a gas concentration measuring module that are capable of preventing inconvenience due to individual differences of the light receiving elements, and preventing inconvenience caused as the element for generating variation in optical path length or a difference in received light energy values is moved in the same direction as the direction of the optical path.

The invention claimed is:

1. A gas concentration calculating device including a gas concentration measuring module and a gas concentration calculating module and configured to calculate a concentration of a target gas,
wherein the gas concentration measuring module comprises:
a gas cell configured to form an introduction space into which the target gas is introduced;
a light source disposed at one end of the gas cell;
a reflection switching unit disposed at the one end or the other end of the gas cell to reflect or transmit light emitted from the light source;
a reflecting unit configured to reflect light transmitted through the reflection switching unit;
a comparison gas cell, in which a predetermined comparison gas is hermetically enclosed, disposed on an optical path of light transmitted through the reflection switching unit; and
a light receiving unit including a single light receiving element, disposed at the other end of the gas cell, and configured to receive, by the single light receiving element both light emitted from the light source, reflected by the reflection switching unit, and passing through the gas cell, and light emitted from the light source, transmitted through the reflection switching unit, passing through the comparison gas cell, reflected by the reflecting unit, and passing through the gas cell, and
wherein the gas concentration calculating module calculates the concentration of the target gas based on received light energy values of the light receiving unit in each case in which light is reflected or transmitted by the reflection switching unit.

2. The gas concentration calculating device according to claim 1, wherein the reflection switching unit is a reflectance modulation unit for electrically modulating a reflectance with respect to light emitted from the light source to switch reflection and transmission of light.

3. The gas concentration calculating device according to claim 2, wherein the reflectance modulation unit is a spatial light modulator.

4. The gas concentration calculating device according to claim 2, wherein the reflectance modulation unit is a liquid crystal optical element.

5. The gas concentration calculating device according to claim 1, wherein the reflection switching unit is a rotary mechanism configured to switch reflection and transmission by rotation with respect to light emitted from the light source.

6. The gas concentration calculating device according to claim 5, wherein the rotary mechanism is a rotating mirror constituted by a reflecting plate and a hole.

7. The gas concentration calculating device according to claim 1, wherein the reflecting unit comprises a plurality of reflecting surfaces, and sequentially reflects light transmitted through the reflection switching unit at the plurality of reflecting surfaces to allow transmission of the light through the comparison gas cell upon each reflection of the reflecting surfaces.

8. The gas concentration calculating device according to claim 1, wherein the predetermined comparison gas is the same kind of saturated gas as the target gas.

9. The gas concentration calculating device according to claim 1, further comprising a band pass filter disposed on an optical path between the light source and the light receiving unit and configured to transmit light having a predetermined wavelength only.

10. The gas concentration calculating device according to claim 1, wherein the light source emits infrared rays.

11. The gas concentration calculating device according to claim 1, wherein the target gas is carbon dioxide.

12. The gas concentration calculating device according to claim 1, comprising the gas concentration measuring module having a plurality of light receiving unit corresponding to different target gases, and the plurality of gas concentration calculating modules corresponding to the plurality of light receiving unit.

13. A gas concentration measuring module of a gas concentration calculating device configured to calculate a concentration of a target gas, the gas concentration measuring module comprising:
a gas cell configured to form an introduction space into which the target gas is introduced;
a light source disposed at one end of the gas cell;
a reflection switching unit disposed at the one end or the other end of the gas cell to reflect or transmit light emitted from the light source;
a reflecting unit for reflecting light transmitted through the reflection switching unit;
a comparison gas cell, in which a predetermined comparison gas is hermetically enclosed, disposed on an optical path of light transmitted through the reflection switching unit; and a light receiving unit including a single light receiving element, disposed at the other end of the gas cell, and configured to receive, by the single light receiving element, both light emitted from the light source, reflected by the reflection switching unit, and passing through the gas cell, and light emitted from the light source, transmitted through the reflection switching unit, passing through the comparison gas cell, reflected by the reflecting unit, and passing through the gas cell.

14. A gas concentration calculating device including a gas concentration measuring module and a gas concentration calculating module and configured to calculate a concentration of a target gas,
wherein the gas concentration measuring module comprises:
a gas cell configured to form an introduction space into which the target gas is introduced;
a light source disposed in the gas cell;
a reflectance modulation unit disposed at one end of the gas cell and configured to electrically modulate a reflectance with respect to light emitted from the light source; and
a light receiving unit including a single light receiving element, disposed at the other end of the gas cell, and configured to receive, by the single light receiving element, both direct light directly emitted from the light source, and passing through the gas cell, and reflection light emitted from the light source, reflected by the reflectance modulation unit and passing through the gas cell, and
wherein the gas concentration calculating module calculates the concentration of the target gas based on a ratio of received light energy values of the light receiving unit in each case in which the reflectance is electrically modulated by the reflectance modulation unit.

15. The gas concentration calculating device according to claim 14, wherein the reflectance modulation unit is an electro-optic device.

16. The gas concentration calculating device according to claim 14, wherein the reflectance modulation unit is a liquid crystal optical element.

17. The gas concentration calculating device according to claim 14, further comprising a band pass filter disposed on an optical path between the light source and the light receiving unit and configured to transmit light having a predetermined wavelength only.

18. The gas concentration calculating device according to claim 14, wherein the light source emits infrared rays.

19. The gas concentration calculating device according to claim 14, wherein the target gas is carbon dioxide.

20. The gas concentration calculating device according to claim 14, further comprising a storage unit for previously storing a database or an approximate equation showing a correlation between the concentration of the target gas and the ratio,
wherein the gas concentration calculating module calculates the concentration corresponding to the ratio based on the database or the approximate equation.

21. The gas concentration calculating device according to claim 14, comprising the gas concentration measuring module having a plurality of light receiving unit corresponding to different target gases, and the plurality of gas concentration calculating modules corresponding to the plurality of light receiving unit.

22. A gas concentration measuring module of a gas concentration calculating device configured to calculate a concentration of a target gas, the gas concentration measuring module comprising:

a gas cell configured to form an introduction space into which the target gas is introduced;
a light source disposed in the gas cell;
a reflectance modulation unit disposed at one end of the gas cell and configured to electrically modulate a reflectance with respect to light emitted from the light source; and
a light receiving unit including a single light receiving element, disposed at the other end of the gas cell, and configured to receive, by the single light receiving element, both direct light directly emitted from the light source, and passing through the gas cell, and reflection light emitted from the light source, and reflected by the reflectance modulation unit, and passing through the gas cell.

23. A gas concentration calculating device including a gas concentration measuring module and a gas concentration calculating module and configured to calculate a concentration of a target gas,
wherein the gas concentration measuring module comprises:
a gas cell configured to form an introduction space into which the target gas is introduced;
a light source disposed in the gas cell;
a rotary mechanism disposed at one end of the gas cell and configured to reflect or transmit light emitted from the light source by rotation thereof; and
a light receiving unit including a single light receiving element, disposed at the other end of the gas cell, and configured to receive, by the single light receiving element, both direct light directly emitted from the light source, and passing through the gas cell, and reflection light emitted from the light source, reflected by the rotary mechanism, and through the gas cell, and
wherein the gas concentration calculating module calculates the concentration of the target gas based on a ratio of received light energy values of the light receiving unit in each case in which the light is reflected or transmitted by the rotary mechanism, and
the rotary mechanism performs the rotation in a direction different from a direction of an optical path from the light source to the light receiving unit.

24. The gas concentration calculating device according to claim 23, wherein the rotary mechanism is a rotating mirror constituted by a reflecting plate and a hole.

25. (Presently Presented): The gas concentration calculating device according to claim 24, wherein the rotating mirror performs the rotation in a direction substantially perpendicular to the direction of the optical path from the light source to the light receiving unit.

26. The gas concentration calculating device according to claim 23, wherein the rotary mechanism is a micro-electromechanical system (MEMS) actuator.

27. The gas concentration calculating device according to claim 23, further comprising a band pass filter disposed on an optical path between the light source and the light receiving unit and configured to transmit light having a predetermined wavelength only.

28. The gas concentration calculating device according to claim 23, wherein the light source emits infrared rays.

29. The gas concentration calculating device according to claim 23, wherein the target gas is carbon dioxide.

30. The gas concentration calculating device according to claim 23, further comprising a storage unit for previously storing a database or an approximate equation showing a correlation between the concentration of the target gas and the ratio, wherein the gas concentration calculating module calculates the concentration corresponding to the ratio based on the database or the approximate equation.

31. The gas concentration calculating device according to claim 23, comprising the gas concentration measuring module having a plurality of light receiving unit corresponding to different target gases, and the plurality of gas concentration calculating modules corresponding to the plurality of light receiving unit.

32. A gas concentration measuring module of a gas concentration calculating device configured to calculate a concentration of a target gas, the gas concentration measuring module comprising:
   a gas cell configured to form an introduction space into which the target gas is introduced;
   a light source disposed in the gas cell;
   a rotary mechanism disposed at one end of the gas cell and configured to reflect or transmit light emitted from the light source by rotation thereof; and
   a light receiving unit including a single light receiving element, disposed at the other end of the gas cell, and configured to receive, by the single light receiving element, both direct light directly emitted from the light source, and passing through the gas cell, and reflection light emitted from the light source, and reflected by the rotary mechanism, and passing through the gas cell,
   wherein the rotary mechanism performs the rotation in a direction different from a direction of an optical path from the light source to the light receiving unit.

\* \* \* \* \*